(12) United States Patent
Harris et al.

(10) Patent No.: US 8,088,884 B2
(45) Date of Patent: Jan. 3, 2012

(54) MULTI-ARMED FORMS OF ACTIVATED POLYOXAZOLINE AND METHODS OF SYNTHESIS THEREOF

(75) Inventors: J. Milton Harris, Huntsville, AL (US); Michael David Bentley, Huntsville, AL (US); Kunsang Yoon, Madison, AL (US); Zhihao Fang, Madison, AL (US)

(73) Assignee: Serina Therapeutics, Inc., Huntsville, AL (US)

( * ) Notice: Subject to any disclaimer, the term of this patent is extended or adjusted under 35 U.S.C. 154(b) by 0 days.

(21) Appl. No.: 12/680,448

(22) PCT Filed: Sep. 29, 2008

(86) PCT No.: PCT/US2008/078159
§ 371 (c)(1),
(2), (4) Date: Apr. 16, 2010

(87) PCT Pub. No.: WO2009/043027
PCT Pub. Date: Apr. 2, 2009

(65) Prior Publication Data
US 2010/0249368 A1    Sep. 30, 2010

Related U.S. Application Data

(60) Provisional application No. 60/975,808, filed on Sep. 27, 2007.

(51) Int. Cl.
*C08G 73/06* (2006.01)

(52) U.S. Cl. .................. 528/423; 424/78.36; 424/178.1; 424/179.1; 424/194.1; 424/280.1; 525/410; 525/411; 525/417; 525/540; 528/403; 528/417; 528/422

(58) Field of Classification Search ............... 424/78.08, 424/78.36, 78.38, 178.1, 179.1, 193.1, 194.1, 424/280.1; 525/410, 411, 417, 540; 528/403, 528/417, 422, 423
See application file for complete search history.

(56) References Cited

U.S. PATENT DOCUMENTS

| | | |
|---|---|---|
| 5,643,575 A | 7/1997 | Martinez et al. |
| 5,932,462 A | 8/1999 | Harris et al. |
| 2010/0069579 A1 | 3/2010 | Harris et al. |

OTHER PUBLICATIONS

Miyamoto, M.; Naka, K.; Shiozaki, M.; Chujo, Y.; Saegusa, T.; Macromolecules, 1990, p. 3201-3205.*

* cited by examiner

*Primary Examiner* — David W Wu
*Assistant Examiner* — Robert Jones, Jr.
(74) *Attorney, Agent, or Firm* — Bradley Arant Boult Cummings, LLP

(57) ABSTRACT

The present disclosure provides novel POZ-2 derivatives, methods for synthesizing POZ-2 derivatives and intermediates useful in such methods. In one embodiment, the POZ-2 derivative comprises two linear POZ chains of the present disclosure linked directly or indirectly to a branching moiety that contains a functional group for linking the POZ-2 derivative to the target molecule. Target molecule-POZ-2 conjugates are also described. In certain embodiment, the POZ-2 derivatives have low polydispersity values and a decreased amount of impurities produced by unwanted side reactions, such as, but not limited to, chain transfer.

16 Claims, 4 Drawing Sheets

Initiation
Propagation
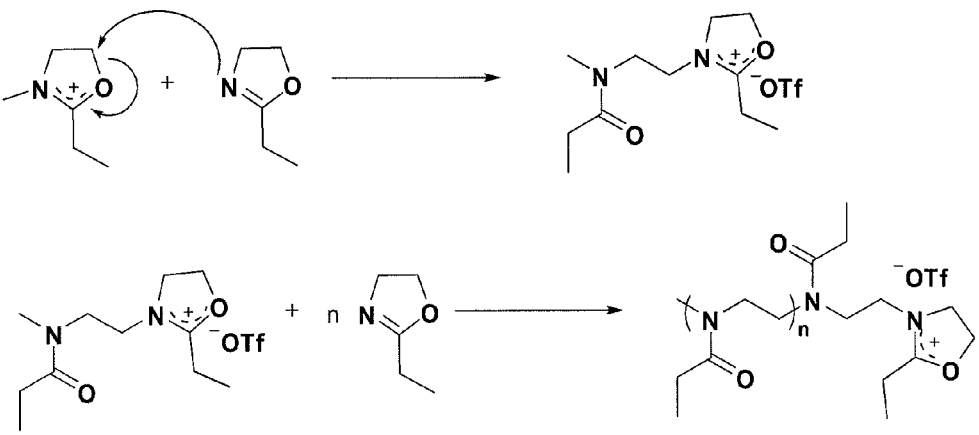
Termination
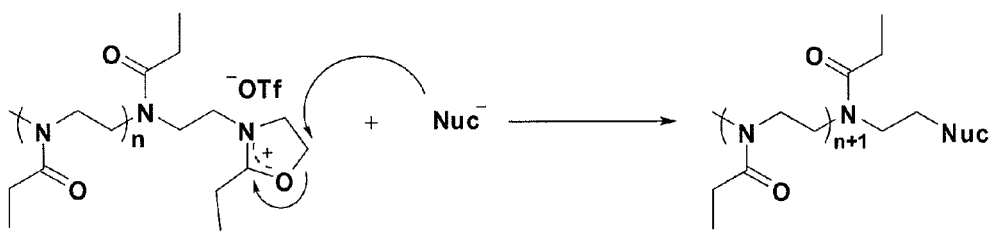
Figure 1. Living-cation mechanism for 2-alkyl-2-oxazoline (i.e. 2-ethyl-2-oxazoline) polymerization where –OTf is –OSO$_2$-CF$_3$ or "triflate" and Nuc⁻ is a negative nucleophile.

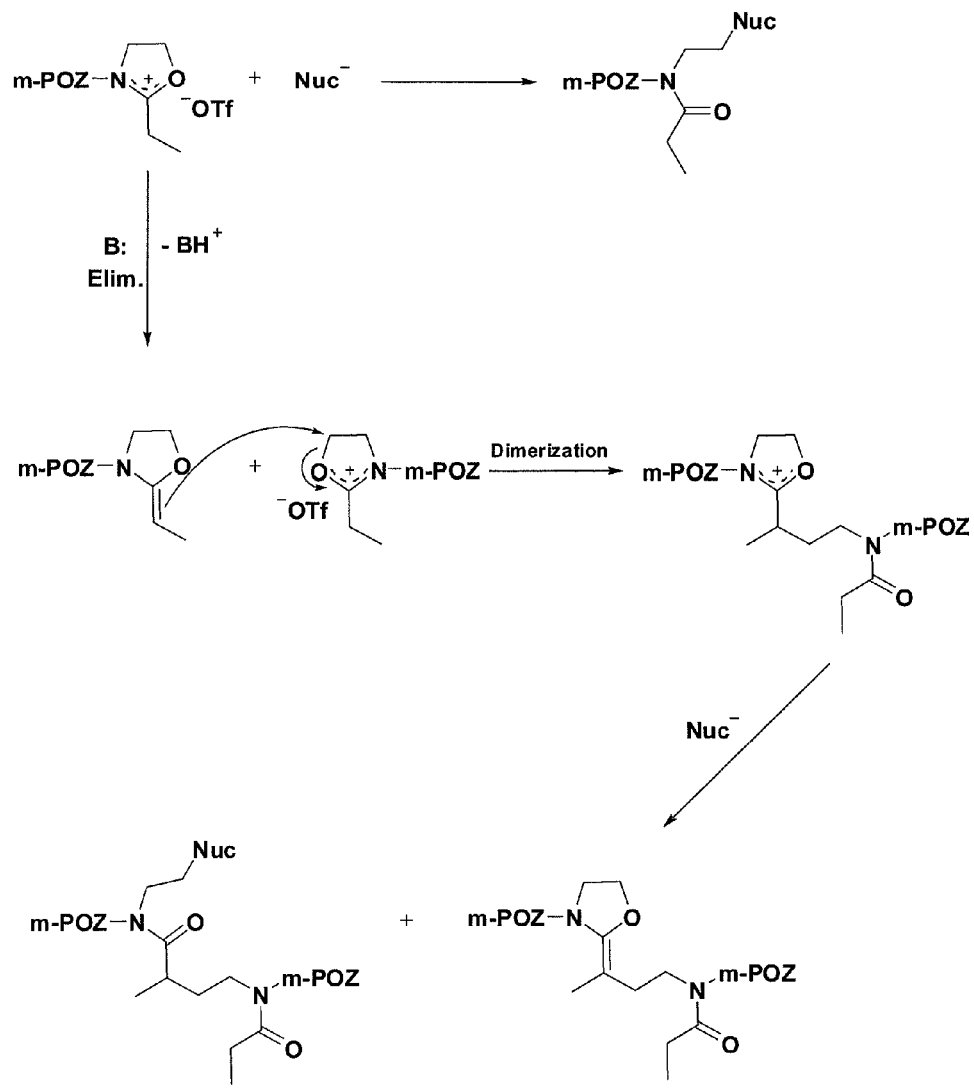
Figure 3. Elimination-dimerization mechanism for chain transfer during polymerization of 2-ethyl-2-oxazoline.

MULTI-ARMED FORMS OF ACTIVATED POLYOXAZOLINE AND METHODS OF SYNTHESIS THEREOF

The present application claims the benefit of U.S. Provisional Patent Application No. 60/975,808, filed Sep. 27, 2008.

FIELD OF THE DISCLOSURE

The present disclosure relates to multiarmed, monofunctional forms of polyoxazolines, methods of synthesis and intermediate compounds useful in producing such polyoxazoline derivatives. Conjugates of such polyoxazoline derivatives with drugs are also described.

BACKGROUND

Polymer-modified therapeutics have proven to be of great utility in modern pharmaceutical science. Due to the success of polymer-modified therapeutics, it is of interest to expand the range of polymers suitable for such applications, especially to provide polymers having properties not possessed by polymers of the prior art. To prepare these therapeutics it is frequently necessary to synthesize water soluble polymers of high molecular weight and high purity. The present disclosure provides branched polyoxazolines which effectively double the available molecular weights and furthermore provide polymers which have low polydispersity and which are monofunctional.

BRIEF DESCRIPTION OF FIGURES

FIG. 1 illustrates the living-cation mechanism for 2-alkyl-2-oxazoline (e.g., 2-ethyl-2-oxazoline) polymerization where —OTf is —OSO$_2$—CF$_3$ or "triflate" and Nuc$^-$ is a negative nucleophile.

FIG. 3 shows a mechanism for the elimination-dimerization mechanism for chain transfer during polymerization of polyoxazoline derivatives, illustrated here as 2-ethyl-2-oxazoline.

DETAILED DESCRIPTION

Definitions

Figure 2A:
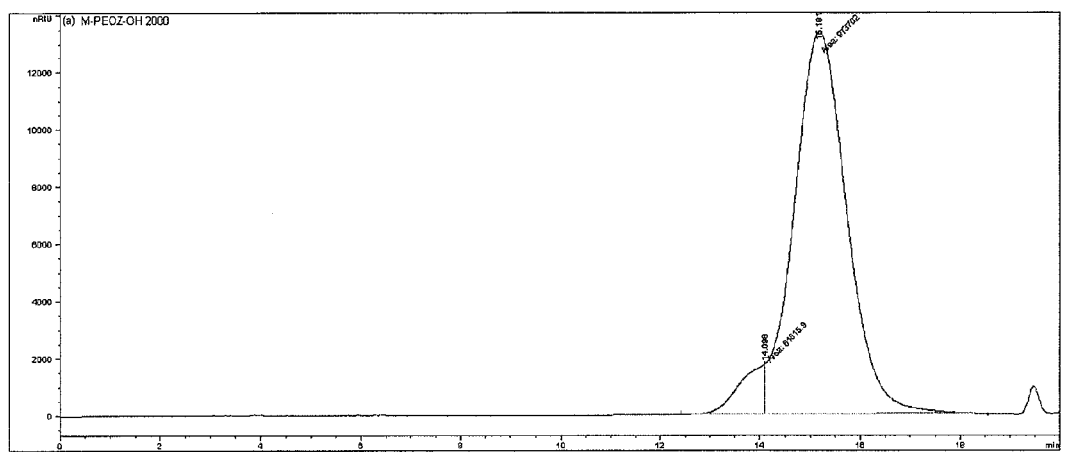
FIGS. 2A and 2B show gel Permeation chromatogram for M-PEOZ—OH 2000 prepared by the methods of the prior art.

As used herein, the term "POZ" "POZ chain" or "POZ derivative" refers to a polymer of 2-substituted-2-oxazoline with the repeating unit having the structure —[N(COR$_2$)CH$_2$CH$_2$]$_n$— in which R$_2$ is independently selected for each repeating unit from an unsubstituted or substituted alkyl, alkenyl, alkyl, aralkyl or aryl group and n is from 3-1000; in one embodiment, the unsubstituted or substituted alkyl, alkenyl or alkynyl groups comprise from 1-10 carbon atoms, such as, but not limited to, methyl, ethyl and n-propyl.

As used herein, the term "POZ-2 derivative" or "polyoxazoline-2 derivative" refers to a molecule having two POZ chains linked, directly or indirectly, through one or more linkages; in certain embodiments, the two POZ chains are linked via a branching moiety.

As used herein, the term "PMOZ" refers to POZ with the repeating unit having the structure —[N(COCH$_3$)CH$_2$CH$_2$]$_n$—.

As used herein, the term "PEOZ" refers to POZ with the repeating unit having the structure —[N(COCH$_2$CH$_3$)CH$_2$CH$_2$]$_n$—.

As used herein, the term M-POZ, M-PMOZ or M-PEOZ refers to the polymers above in which the terminal nitrogen is bound to methyl.

As used herein, the term "monofunctional POZ-2 derivative" or "monofunctional polyoxazoline-2 derivative" refers to POZ-2 derivative having a single active group linked, directly or indirectly through one or more linkages, to one or both POZ chains of the POZ-2 derivative and capable of forming a linkage with a chemical group on a target molecule.

As used herein, the term "target molecule" refers to any molecule having therapeutic or diagnostic application comprising a binding partner that is capable of reacting with a POZ-2 derivative (which may be a monofunctional POZ-2 derivative) of the present disclosure; target molecules include, but are not limited to, a drug, a diagnostic agent, an organic small molecule, an oligonucleotide, a polypeptide, and a protein.

As used herein, the term "hydrolytically stable target molecule-POZ-2 conjugate" refers to a conjugate of a POZ-2 derivative, which may be a monofunctional POZ-2 derivative, and a target molecule such that all the chemical linkages in the conjugate are hydrolytically stable.

As used herein, the term "hydrolytically stable" refers to a linkage that is stable in aqueous solutions under physiological conditions; in one embodiment, such linkages are stable for at least 12 hours, 24 hours, 48 hours, 96 hours, 192 hours or greater; in an alternate embodiment such linkages are stable indefinitely.

As used herein, the term "hydrolytically unstable" refers to a linkage that is not stable in aqueous solutions under physiological conditions.

As used herein, the term "physiological conditions" refers to an aqueous solution having a pH from 6-8 and a temperature from 30-42° Celsius.

As used herein, the term "active" refers to those functional groups that react readily with electrophilic or nucleophilic groups, in contrast to those functional groups that require strong catalysis or impractical reaction conditions in order to react.

As used herein, the term "link", "linked" "linkage" or "linker" when used with respect to a POZ derivative described herein, or components thereof, refers to groups or bonds that normally are formed as the result of a chemical reaction and typically are covalent linkages.

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

As used herein, the term "alkyl", whether used alone or as part of a substituent group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$ CH(CH$_3$)$_2$, —CH$_2$CH(CH$_3$)(CH$_2$CH$_3$), —CH$_2$CH (CH$_2$CH$_3$)$_2$, —CH$_2$C(CH$_3$)$_3$, —CH$_2$C(CH$_2$CH$_3$)$_3$, —CH (CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$) CH$_2$CH(CH$_3$)$_2$, —CH(CH$_3$)CH(CH$_3$)CH(CH$_3$)CH(CH$_3$)$_2$, —CH(CH$_2$ CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl", and "unsubstituted alkynyl" refers to alkyl, alkenyl and alkynyl groups that do not contain heteroatoms.

The phrase "substituted alkyl", "substituted alkenyl", and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, and nitriles; a silicon atom in groups such as in trialkylsilyl groups, dialkylarylsilyl groups, alkyldiarylsilyl groups, and triarylsilyl groups; and other heteroatoms in various other groups. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)-amine, (aryl)(heterocyclyl)amine, or diheterocyclylamine group.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus; the phrase "substituted aryl" includes, but is not limited to tolyl, and hydroxyphenyl among others.

As used herein, the term "unsubstituted aralkyl" refers to unsubstituted alkyl groups as defined above in which a hydrogen or carbon bond of the unsubstituted alkyl group is replaced with a bond to an aryl group as defined above. For example, methyl (CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" refers to an unsubstituted heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

As used herein, the term "substituted heterocyclylalkyl" has the same meaning with respect to unsubstituted heterocyclylalkyl groups that substituted alkyl groups had with respect to unsubstituted alkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

General Description

Polyoxazolines (POZ) are polymers prepared from 2-substituted-2-oxazoline monomers, such as, but not limited to, 2-alkyl-2-oxazoline and 2-aryl-2-oxazoline monomers. When the alkyl group is ethyl or methyl, these polymers are water soluble and have been reported to be nontoxic in mammalian model systems. POZ is generally prepared by reaction of the appropriate stoichiometric amount of 2-substituted-2-oxazoline with an electrophilic initiator, such as methyl p-toluenesulfonate (or "tosylate") or methyl trifluoromethanesulfonate (or "triflate"), followed by termination with a nucleophile such as hydroxide, FIG. 1. The polymer produced is conveniently described in shorthand with the initiating group designated by the leftmost group and the terminating group designated by the rightmost group, with the 2-substituted-2-oxazoline component in the middle. Therefore, when this shorthand description is used in the current specification, it is intended that the left side of the designation presents the "initiator end" and the right side of the designation presents the "termination end", unless designated otherwise. For example, when the 2-substituted-2-oxazoline is 2-methyl-2-oxazoline, methyl tosylate is used as the initiator and hydroxide is used as the terminator, the following POZ is produced:

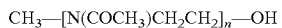

The polymer above is conveniently described in shorthand notation as M-PMOZ—OH, in which the methyl initiator is designated by the leftmost M, PMOZ represents polymethyloxazoline with the methyl of the repeating unit designated by the M of PMOZ, and the terminating hydroxyl is designated by —OH.

Another commonly used monomer is 2-ethyl-2-oxazoline, which with methyl tosylate initiation and piperazine ($HNC_4H_8NH$) termination provides M-PEOZ—$NC_4H_8NH$, where E represents the ethyl group.

The degree of polymerization, n, can range from approximately 3 to about 1000.

Occasionally it will be necessary to reverse the shorthand notation to indicate that the initiator end of the polymer is on the right and the terminator end is on the left. This can be done by adding a prime, as in PMOZ'. Thus, our usual notation for a PMOZ initiated with methyl and terminated with hydroxyl is M-PMOZ—OH. This same polymer will be drawn in reverse form in shorthand as HO-PMOZ'-M.

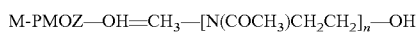

Oxazoline polymerization can also be initiated with electrophiles that possess additional functional groups not involved in initiation of polymerization. For example the electrophilic initiator ethyl 3-bromopropionate has been used to initiate 2-ethyl-2-oxazoline polymerization. Termination with hydroxide gives the following polymer:

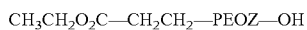

Yet another route to preparing polyoxazolines with functional groups is to copolymerize a monomer such as 2-ethyl-2-oxazoline with an oxazoline monomer having a functional group in the 2-position. For example, Jordan and colleagues have prepared oxazolines with acetylenes and protected aldehydes, carboxylic acids and amines in the 2-position (F. C. Gaertner, R. Luxenhofer, B. Blechert, R. Jordan and M. Essler, J. Controlled Release, 2007, 119, 291-300). Copolymerization of these functional monomers with 2-ethyl-2-oxazoline gives polyoxazolines with multiple pendant or side-chain functional groups. The above POZ compounds have the potential to be coupled to target molecules such as, but not limited to, proteins and small molecule drugs.

The art has recognized that one shortcoming of POZ derivatives with pendant or side chain functional groups is that these preparations provide multiple functional groups allowing crosslinking and aggregate formation when coupling with multi-functional target molecules, such as, but not limited to, polypeptides and proteins. Techniques for preparing monofunctional polymers using pendant side chains have not been described. A monofunctional polymer is useful in preparation of polymer therapeutics. Also there are some instances when one would desire to have a single molecule coupled to a polymer. For these purposes, the multifunctional POZ derivatives generated using an oxazoline monomer having a functional group in the 2-position would not be acceptable.

Work with polyethylene glycol has shown that it is frequently necessary in modification of target molecules by polymers to utilize polymers of molecular weights (MWs) of 20,000 Da or higher and molecular weight distributions, or polydispersities (PDs), of less than 1.1. There has been a great deal of work showing that MWs and PDs in the above range cannot be achieved for POZ polymers with conventional techniques. It is generally seen that as the molecular weight of growing POZ chains reaches approximately 5,000 Da, the polydispersity increases appreciably. Side reactions, including, but not limited to, chain transfer, begin to grow in importance. The prior art techniques described above when applied to POZ derivatives of high MW produce POZ derivatives with unacceptable PD values. The prior art has identified certain techniques to produce high MW POZ derivatives with acceptable PD values; however, these techniques are not applicable to large scale, commercial use. For example, the use of very low polymerization temperatures combined with reaction times of several days or weeks has been shown to give acceptable PDs, but such conditions are not practical for commercial-scale preparations (J. S. Park and K. Kataoka, Macromolecules, 39, 6622 (2006)). Hoogenboom, Schubert and colleagues indicate that low-PD POZ can be prepared by using microwave irradiation, but again commercial-scale polymerizations are not currently practical with this technique (R. M. Paulus, T. Erdmenger, C. R. Becer, R. Hoogenboom and U.S. Schubert, Macromol. Rapid Comm., 28, 484-491 (2007)). As a consequence, the POZ compounds described to date by the art are seriously limited for use in polymer therapeutics.

One approach utilized to obtain high molecular weights for polyethylene glycols is to couple two linear polyethylene glycol chains to a branching point (see Ji, US Patent Application Publication US 2005/0180946; Harris, U.S. Pat. No. 5,932,462; Martinez, U.S. Pat. No. 5,643,575). However, the chemistry of POZ formation, such as, but not limited to, the chain transfer reaction, prevents the straightforward extension of polyethylene glycol chemistry to POZ. Therefore, new methods of synthesis are needed in the art to produce POZ derivatives with high molecular weight and low PD values suitable for use in pharmaceutical and other applications.

Yet another problem hindering use of POZ derivatives in modification of target molecules is the removal of a positively charged group when a POZ derivative is used that comprises an active ester or active carbonate group (two of the most common forms of active, functional polymer derivatives) for forming a conjugate with a target molecule, such as, but not limited to, polypeptides and proteins. This loss of charge results from conversion of a protein amine to a non-basic amide or urethane. It has been proposed that the loss of a positive charge on a protein can affect the activity of the proteins/polypeptides.

Summary of the Current Disclosure

The present disclosure avoids the above limitations of current methods of synthesis for POZ-2 derivatives and provides novel POZ-2 derivatives, intermediates useful in such synthesis and target molecule-POZ-2 derivative conjugates.

The present disclosure provides novel methods for synthesizing POZ derivatives with low PD values and a decreased amount of impurities produced by unwanted side reactions, such as, but not limited to, chain transfer. In one embodiment, the present disclosure describes novel methods for minimizing unwanted side reactions, such as, but not limited to, chain transfer, allowing the production of POZ derivatives of increased purity with low PD values. In one embodiment, the methods of the present disclosure provide for POZ derivatives with low PD values at increased MW values. In a further embodiment, POZ derivatives are produced with no or decreased amount of impurities. The novel methods provided for in the present disclosure are an improvement over the methods of the prior art and provide for large scale commercial preparation of POZ derivatives suitable for use in modification of a wide variety of target molecules.

Therefore, the present disclosure also provides POZ derivatives of increased purity and with low PD values suitable for use in pharmaceutical applications. In a particular embodiment, the methods of the present disclosure provide for POZ derivatives with low PD values at increased MW values. As is known in the art PD values will vary with MW; in general, as the molecular weight increases the PD value also increases. Using the methods of the present disclosure, POZ derivatives of various MWs can be produced with lower PD values at a given MW than can be produced using the methods of the prior art. For example, using the methods of the present disclosure, POZ derivatives of 20,000 Da MW or less can be produced with PD values of less than or equal to 1.1. In a further particular embodiment, POZ derivatives are produced with no or decreased amount of impurities. As is known in the art and illustrated in the Examples herein, POZ derivatives synthesized using the methods of the prior art exhibit certain impurities that are seen as high MW shoulders and low MW tails. These impurities are generated, at least in part, through unwanted side reactions, such as, but not limited to, chain transfer. As a result, the disclosed POZ derivatives are suitable for use in modification of a wide variety of target molecules and for incorporation into POZ-2 derivatives of the present disclosure.

The present disclosure also provides for POZ-2 derivatives which are branched as compared to linear POZ derivatives as previously known in the art. In one embodiment, the POZ-2 derivative comprises two linear POZ chains of the present disclosure linked together through a novel branching moiety that contains a functional group, which may be a monofunctional group, for linking the POZ-2 derivative to the target molecule. In this manner a hydrolytically-stable conjugate is formed between the target molecule and POZ-2. In a particular embodiment, at least one of the POZ components of the POZ-2 derivative is a POZ derivative of the present disclosure with a low PD value. Therefore, the present disclosure provides an effective approach to doubling the MW of POZ chains conjugated to a target molecule by using a POZ-2 derivative of the present disclosure. Such an approach provides the above-mentioned benefits with a smaller increase in PD as compared to using a single chain POZ derivative of the same MW and allows the manufacture of such POZ derivative in a commercially relevant manufacturing process. In a particular embodiment, the one or more nitrogen branch points can provide a basic site that can act to prevent loss of a positive charge on the target molecule when a POZ-2 derivative contains an active ester or carbonate for coupling to target molecules.

Methods of Synthesis of POZ Derivatives with Low PD Values

The current state of the art for polymerization of 2-substituted-2-oxazolines, including, but not limited to, 2-aryl- and 2-alkyl-2-oxazolines is derived from the publications of Kobayshi, Nuyken and Jordan (S. Kobayashi, E. Masuda, S. Shoda and Y. Shimano, Macromolecules, 1989, 22, 2878-2884; A. Gross, G. Maier and O. Nuyken, Macromol. Chem. Phys., 1996, 197, 2811-2826; and F. C. Gaertner, R. Luxenhofer, B. Blechert, R. Jordan and M. Essler, J. Controlled Release, 2007, 119, 291-300). In these methods polymerization is initiated with an electrophile, such as an alkyl tosylate or alky triflate; in one embodiment, methyl tosylate or methyl triflate is used. These strong electrophiles are used to favor polymerization by a living-cation mechanism since this mechanism, in theory, gives no termination or chain-transfer reactions (Q. Liu, M. Konas and J. S. Riffle, Macromolecules, 1993, 26, 5572-5576) (see FIG. 1). However, it is known from the prior art that chain transfer reactions do occur and that the reaction does not proceed strictly by the living cation mechanism. If weak electrophiles such as, but not limited to, alkyl halides are used, the reaction proceeds by a covalent mechanism with a consequent significant increase in PD. The prior art polymerization methods utilize chlorobenzene, dichlorobenzene or acetonitrile as solvent. The propagation phase is conducted at approximately 80° C. for approximately 1-3 days. Termination is conducted by heating at 80-90° C. with aqueous sodium carbonate to give a hydroxyl terminal group or by reacting with a secondary amine such as morpholine or piperidine to give a terminal tertiary amine.

The use of these typical, prior art methods leads to the presence of a high-MW shoulder of approximately 5-10% and significant low-MW tailing in gel permeation chromatography. Such results have been noted in the art (see J. Park and K. Kataoka, Macromolecules, 2006, 39, 6622-6630.). It is generally stated in the literature that this broadening of the MW distribution is due to chain transfer proceeding through an elimination-dimerization mechanism, although structural details and experimental support for this process are limited (M. Litt, A. Levy and J. Herz, J. Macromol. Sci.-Chem., 1975, A9, 703-727). To the extent that chain transfer reactions do occur, such reactions cannot be considered to be truly living polymerizations. Therefore, it would be beneficial to reduce the occurrence of unwanted side reactions such as chain transfer.

The applicants have clarified the details of the elimination-dimerization mechanism, provided experimental support for the mechanism, and proposed implications of the mechanism regarding the termination step. This latter advance is particularly important because it shows why certain termination reactions fail and it leads us to choose termination reactions that succeed. Such a finding has not been described in the art and it provides guidance in creating synthetic methods that minimize the occurrence of unwanted side reactions and that yield the desired terminated products.

As discussed herein, the use of the prior art methods produced a POZ product that contained a high MW shoulder of approximately 5-10% of the total mass of the POZ product. This high MW shoulder contributes to the unacceptable PD values obtained using synthetic methods of the prior art. The high MW shoulder observed in the methods of the prior art is composed, at least in part, of a high-MW dimer that is formed during the polymerization and/or termination steps (see FIG. 3). The elimination-dimerization mechanism predicts that if chain transfer occurs during the termination step, the material in the high MW shoulder would be approximately double the MW of the desired product. Furthermore, if chain transfer occurs during the propagation step, a new polymer chain will be initiated, and since monomer concentration is less at this point, the MW of this polymer will be less than that of the bulk of polymer. In addition, since this new polymer chain results from chain transfer, it must be initiated by a proton, rather than by methyl, and thus the MALDI spectrum of this polymer will show a set of peaks 14 Da less than that of the main peak.

There are implications regarding the termination step as well, which have not been appreciated to date. For example, the addition of a terminating nucleophile which is a strong base and weak nucleophile is predicted to result in significant elimination and dimerization. Furthermore, the oxazolinium cation is a delocalized or "soft" electrophile, and theory predicts that a "soft" or diffuse nucleophile would be more likely to act as a terminating nucleophile than as a base. As an example, one would expect a "soft" mercaptide to be a more effective terminating agent than a "hard" alkoxide.

The above predictions were confirmed experimentally. In one example, sterically hindered ethyldiisopropylamine (a strong base and weak nucleophile) was added to terminate 2-ethyl-2-oxazoline polymerization. This reaction resulted in an increase of high MW dimer product to 75% (see Example 3). It was confirmed that the MW of the impurity peak in GPC is approximately double that of the MW of the desired product. In addition, the MALDI-TOF spectrum confirmed that a portion of the main peak exhibited a second set of peaks that are 14 mass units less than expected. We have observed that the MW of this second set of peaks is somewhat less than twice that of the desired product. Presumably this occurs because some chain transfer takes place during the propagation phase before polymer is fully formed and monomer is depleted; in this case the base must be monomer since it is the strongest base present during propagation.

In addition, termination by alkoxides, which are known as hard nucleophiles, leads to significant amounts of high MW dimer with no product derived from the desired nucleophilic attack (see Example 5). In addition, termination by mercaptides, which are known as soft nucleophiles, does, as predicted, lead to the desired product of nucleophilic attack (see Example 11).

As a result of the foregoing observations, the applicants have developed novel synthetic methods that reduce unwanted side reactions, such as chain transfer, and allow the production of POZ polymers and derivatives with superior properties as compared to the prior art. The improved methods may utilize one or more of the following improvements.

In one embodiment, the POZ polymerization reaction is initiated with a strong electrophile such as, but not limited to, alkyl tosylate or alkyl triflate; in one embodiment, methyl tosylate or methyl triflate are used.

The elimination-dimerization mechanism also suggests that both propagation and termination should be conducted at low temperature since bimolecular eliminations are favored by high temperatures. The Examples confirm this observation by showing that high MW dimer formation is reduced by lowering temperature of both propagation and termination. This prediction has also been confirmed by Kataoka (see J. Park and K. Kataoka, Macromolecules, 2006, 39, 6622-6630). However, if one lowers the temperature sufficiently to eliminate all chain transfer it can take weeks to reach completion of the reaction, and thus such reactions are not commercially viable. The present disclosure describes methods below which are commercially viable. We have observed that continuing heating after propagation is complete or nearly complete will cause a buildup in elimination-dimerization. The present disclosure has surprisingly found that POZ derivative quality is greatly improved by terminating the polymerizations much earlier and at lower temperatures than in the state-of-the-art methods. In addition, the duration of the propagation reaction is the minimum time required for complete or substantially complete (greater than or equal to 90%) monomer consumption. It should be noted that the temperature and the duration of the propagation reaction are interrelated. In other words, higher propagation temperatures may be used with shorter propagation reaction times. Conversely, if longer propagation reaction times are used, the temperature should be reduced accordingly.

It has also been found that the use of solvents, such as but not limited to, chlorobenzene, provide faster polymerization than the commonly used acetonitrile solvent, which is critical for commercial, large scale preparations of POZ products. While the prior art has recognized chlorobenzene as solvent, the improvement in reaction rates has not been recognized. The unexpected result that using chlorobenzene as a solvent provides faster reaction times allows the polymerization reaction to be terminated earlier and at higher temperatures without increasing the formation of high MW dimer products. Such an improvement was not appreciated in the art.

Furthermore, filtration of POZ products, especially those terminated with OH groups, through cation-exchange resins improves PD values. It is believed that such filtration removes low-MW and high-MW products. The effect of filtration is especially significant for higher molecular weight POZ products (for example, those products of 10,000 Da and above); however, filtration provides benefits for POZ derivatives regardless of MW. To give one example of this improvement, unfiltered M-PEOZ—OH 10,000 (produced by the methods of the present disclosure) showed Mn 7950 Da and PD 1.21 (GPC), with a significant low-MW tail. Filtration of this product through carboxyethyl-Sepharose gave Mn 9180 Da and PD 1.05 (from GPC) and Mn 9780 and PD 1.01 (from MALDI), with no observable low-MW tailing and a slight 2% high-MW shoulder (as determined by GPC). The fact that the high-MW shoulder was not revealed for the crude product shows that the cation-exchange filtration removed high-MW as well as low-MW impurities.

Furthermore, in certain cases if the POZ product comprises a carboxylic acid as the terminal group, anion-exchange chromatography can be used to isolate the desired product and remove any high molecular weight products that are formed. We have conducted this experiment for M-PEOZ—S—$CH_2CH_2$—$CO_2H$. It is noteworthy that this chromatography experiment showed that the high-MW dimer was neutral. Hence the major dimerization product must be the alkene of FIG. 3. In this experiment, the crude product had Mn of 9600 Da, PD of 1.09 (GPC) and 6% high-MW shoulder. After anion-exchange chromatography on DEAE-Sepharose, Mn was 9500 Da, PD was 1.06 (GPC), and there was no high-MW shoulder.

In an additional embodiment, the termination reaction is conducted at a low temperature (in one embodiment, less than 80° C.; in an alternate embodiment from 15 to 40° C.) and with a nucleophile which is a better nucleophile than it is a base; exemplary nucleophiles include, but are not limited to, soft nucleophiles such as mercaptides. The applicants have found that the use of sodium alkoxide compounds as terminating agents does not produce the desired products; rather, the unterminated cation remains. However, the use of sodium mercaptides and related compounds, such as, but not limited to, NaS—$CH_2CH_2$—$CO_2Et$, give effective termination and yields POZ products with desired properties, such as but not limited to, low PD values. Hydrolysis of this ester to the carboxylic acid, followed by anion-exchange chromatography, gives high quality POZ product with low PD values and with no high-MW shoulder. In one such example M-PEOZ—S—$CH_2CH_2$—$CO_2H$ of Mn 9600 Da, PD of 1.09 (GPC), and 6% shoulder was produced. Anion-exchange chromatography on DEAE-Sepharose gave Mn 9500, PD 1.06 (GPC) and no shoulder.

These novel improvements in synthesis may be utilized in the preparation of the POZ chains and POZ-2 derivatives described herein. As would be obvious to one of ordinary skill in the art, the improvements in synthesis may be used in various combinations; the foregoing should not be interpreted as requiring each of the improvements to be used in a given synthesis.

The methods of the prior art were used to synthesize M-PEOZ—OH 2000 by two methods. The description of the synthesis of these POZ derivatives is provided in Example 1 (for FIG. 2A) and Example 2 (for FIG. 2B). The produced POZ derivatives were analyzed. For the POZ derivative of FIG. 2A, GPC showed a single peak with an appreciable high-MW shoulder (Mn=3600 Da, 9%). The main peak had a Mn of 1980 Da, PD 1.08. NMR showed the expected peaks (see Example 6). MALDI-TOF MS gave a set of peaks with a maximum at 2000 Da, PD 1.04 and 99.1 Da separation. The MALDI spectrum also showed a second set of peaks with 99.1 Da separation, but with each peak 14 Da less than the main set. The maximum for this set of peaks occurred at 1600 Da. For the POZ derivative of FIG. 2B, GPC showed a single peak with an appreciable high-MW shoulder (Mn=3300 Da, 6%). The main peak had a Mn of 2200 Da, PD 1.06. NMR showed the expected peaks (see Example 6). MALDI-TOF MS gave a set of peaks with a maximum at 2300 Da, and 99.1 Da separation. The MALDI spectrum also showed a second set of peaks with 99.1 Da separation, but with each peak 14 Da less than the main set. The maximum for this set of peaks occurred at 2100 Da.

Figure 4A:
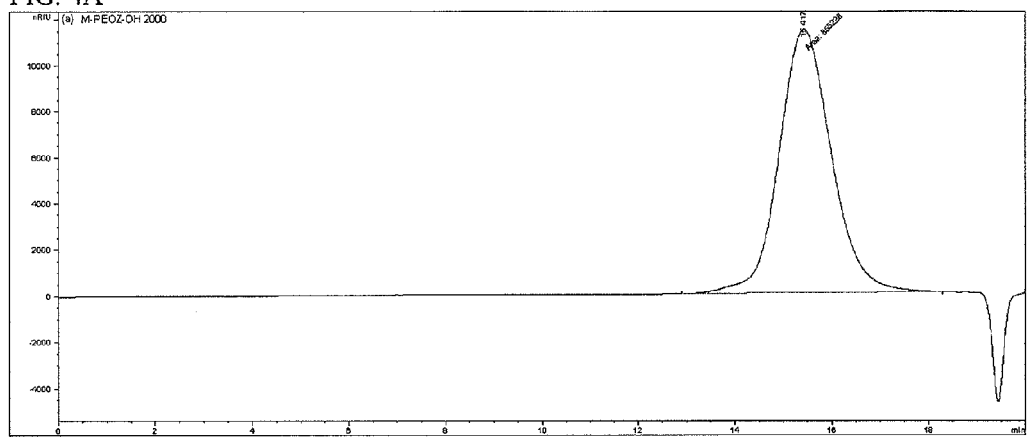
FIGS. 4A and 4B shows gel permeation chromatogram for M-PEOZ—OH 2000 (FIG. 4A) and M-PEOZ—OH 5000 (FIG. 4B) prepared by optimized condition of current invention.
Figure 4B:
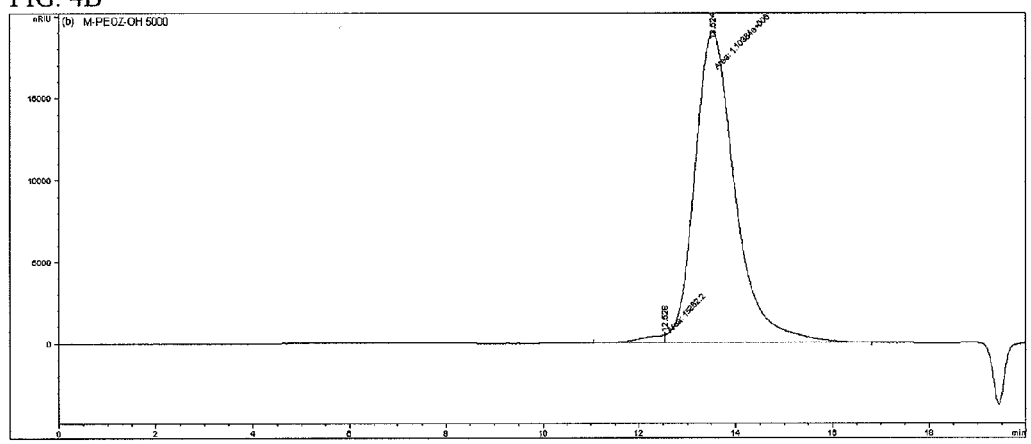

The methods of the present disclosure were used to synthesize two POZ derivatives, M-PEOZ—OH 2000 (FIG. 4A) and M-PEOZ—OH 5000 (FIG. 4B) for comparison. The description of the synthesis of these POZ derivatives is provided in Example 6 (for FIG. 4A) and Example 7 (for FIG. 4B). The GPC chromatograms are provided in FIGS. 4A and 4B. FIGS. 4A and 4B show the greatly improved GPCs of M-PEOZ—OH 2000 and 5000 obtained using the synthesis methods of the present disclosure. For M-PEOZ 2000 the reaction conditions were: (a) methyl triflate initiation, propagation in chlorobenzene at 110° C. for 1.5 hours, and termination at room temperature with aqueous carbonate. The M-PEOZ 2000 derivative was observed to have a Mn of 1900 Da (from MALDI and GPC), a PD of 1.07 (GPC) and 1.03 (MALDI) and no high-MW shoulder and no low-MW tail.

For M-PEOZ—OH 5000 the reaction conditions were: (a) methyl triflate initiation, propagation in chlorobenzene at 42° C. for 1 hour and then 80° C. for 3.75 hours, and termination at room temperature with aqueous carbonate. The M-PEOZ 5000 derivative was observed to have a Mn of 4900 Da (from MALDI), a PD of 1.06 (GPC) and 1.02 (MALDI), a very slight high-MW shoulder (1%) and no low-MW tail. M-PEOZ—OH 10,000 prepared under similar conditions gave Mn of 9780 Da (MALDI), PD of 1.01 (MALDI) and 1.05 (GPC), and a very slight high-MW shoulder of 2%.

In summary, the applicants have identified the nature of the unwanted side reactions that occur when using the synthesis methods of the prior art thereby allowing the applicants to identify reaction conditions that minimize the contribution of such side reactions. As a result, the methods of the present disclosure allow for the preparation of POZ chains and POZ-2 derivatives with superior properties over those available in the art. In one embodiment, the methods of the present disclosure allow for the preparation of POZ chains and POZ-2 derivatives with low PD values; in a particular embodiment, the methods of the present disclosure allow for the preparation of chains and POZ-2 derivatives with low PD values at high MW values. In addition, the methods of the present disclosure allow the production of the foregoing in a manner suitable for large scale production. Such POZ chains and POZ-2 derivatives with such characteristics, as well as methods for producing the same have been lacking in the art.

In one embodiment, the methods of the present disclosure provide such benefits in POZ synthesis by providing a reduction, either completely or partially, of one or more side reactions that occur during the initiation, polymerization or termination processes of POZ synthesis. In a particular embodiment, the side reaction is the chain transfer process. Such unwanted side reactions, such as, but not limited to, the chain transfer process, are a problem in current state of the art procedures for manufacturing POZ products. Such side reactions provide POZ derivatives with unwanted characteristics, such as high PD values.

POZ-2 Derivatives

In its simplest form, the "POZ-2" derivatives of the present disclosure can be represented as follows:

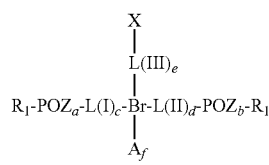

where $POZ_a$ and $POZ_b$ are each a polyoxazoline derivative (as described above) which are linked to a branching moiety, indicated as Br, and X is a functional group or a molecule containing a functional group that is linked to Br, wherein the functional group is capable of reacting with a binding partner on a target molecule or capable of being activated to permit react with a binding partner on a target molecule. Br is the branching moiety and may be a nitrogen atom, a carbon atom or a substituted or unsubstituted aryl group. Combinations of the foregoing may also be used. A is a non-reactive group, including, but not limited to, H and substituted and unsubstituted alkyl groups. $POZ_a$, $POZ_b$ and X may be linked directly to Br or may be linked to Br via linking moieties L(I), L(II) or L(III), respectively. In the above formula, c, d and e are each independently 1 or zero and f is zero when Br is a nitrogen atom or substituted or unsubstituted aryl group and is 1 when Br is a carbon atom. In one embodiment, L(I), L(II) and L(III) are each independently selected from —O—CO—NH—, —CO—NH—, substituted or unsubstituted alkyl groups or substituted or unsubstituted alkenyl groups. Exemplary groups include, but are not limited to, —$(CH_2)_x$—, —$(CH_2)_x$—O—CO—NH— and —$(CH_2)_x$—CO—NH— (where x=1-10); other linking groups described herein may also be used. For the sake of clarity, the presence of L(I), L(II) and L(III) are optional.

In one embodiment, when Br is a carbon atom, at least one of a or b is 1 and the corresponding linking group is or contains a substituted or unsubstituted aryl group. In certain embodiments, both a and b are 1 and at least one of the linking groups L(I) and L(II) is or contains a substituted or unsubstituted aryl group.

As can be seen, the new POZ compounds can be described as "two-armed" POZ derivatives or simply as "POZ-2" derivatives. The individual linear POZ chains, $POZ_a$ and $POZ_b$, comprising the POZ-2 derivative may be the same or may be different and may have the same or different lengths. In one embodiment, at least one of the individual linear POZ chains are linear POZ chains having low PD values as described herein. In an alternate embodiment, each of the individual linear POZ chains are linear POZ chains having low PD values as described herein. Other linear POZ chains are described in U.S. Application No. 60/892,212 and Patent Cooperation Treaty Application No. PCT/US2008/002626, each of which are hereby incorporated by reference as if fully set forth herein. In some instances the POZ will be directly linked to the branching moiety, but in other instances there will be linking groups between the branching moiety and POZ. Similarly, there may be a linking group between the branching moiety and the reactive functional group X.

The POZ-2 derivatives of the present disclosure can be manufactured using a variety of methods as disclosed herein. The present disclosure provides several POZ-2 derivatives and methods to synthesize the described POZ-2 derivatives. In certain embodiments, the POZ-2 derivatives are monofunctional POZ-2 derivatives. In one embodiment, these routes utilizes the at least one of the optimized conditions for synthesis of the preformed POZ chains described in the preceding section. In a specific embodiment, the POZ chains incorporated into the POZ-2 derivative have improved properties over the prior art, such as, but not limited to, lower PD values at a given MW than POZ chains produced using the methods of the prior art.

Method A—Reaction of Preformed POZ Derivatives with a Nitrogen Branching Moiety

In certain embodiment, the POZ-2 derivatives incorporate a nitrogen atom or a nitrogen containing compound as the branching moiety. In each of the embodiments below, the POZ-2 derivative may be a monofunctional POZ-2 derivative. Furthermore, in each POZ-2 derivative embodiments shown below, the POZ-2 derivatives may form a hydrolytically stable target molecule-POZ-2 conjugate.

A general representation for the POZ-2 derivatives generated by the current method is shown as follows:

Where P is a linking moiety including, but not limited to, —NHCO$(CH_2)_x$—, —NH$(CH_2)_x$—, —OCONH$(CH_2)_x$—, —O$(CH_2)_x$—, —O$_2$C—$(CH_2)_x$—, —O$(CH_2)_y$CONH$(CH_2)_x$—, —NHCSO$(CH_2)_x$—, —$(CH_2)_x$— where x and y are independently selected from 1-10, and

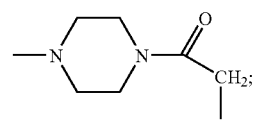

where A is a linking moiety, including, but not limited to, —CO$(CH_2)_z$—, and —$(CH_2)_z$— where z is 1-10.

Z is a functional group, including, but not limited to, carboxylic acid, active esters, carbonates, aldehyde, oxyamine, acetylene, isocyanates, isothiocyanate, amines, alcohol, tresylate (2,2,2-trifluorethylsulfonate), vinylsulfone, iodoacetamide, pyridyldisulfide, ketones, azide, hydrazide, and maleimide, which are capable of forming a linkage with a target molecule or being converted to a group that will form a linkage with a target molecule;

N is a nitrogen atom;

POZ is a polyoxazoline of formula $[N(COR_2)CH_2CH_2]_n—$;

$R_1$ is independently selected for each POZ chain from hydrogen, an alkyl, substituted alkyl, aralkyl, or substituted aralkyl group;

$R_2$ is independently selected for each repeating unit of POZ from an unsubstituted or substituted alkyl, alkenyl, alkyl, aralkyl or aryl group;

n is independently selected for each POZ chain from 3 to 1000; and p is independently selected for each POZ chain from one or zero.

Exemplary embodiments of this method of synthesis are provided below. One straightforward route to the synthesis of POZ-2 derivatives is to react a high quality POZ derivative containing a terminal amine with a small molecule amine containing two carboxylic acid groups or N-hydroxysuccinimidyl active esters (referred to as "NHS"). For example:

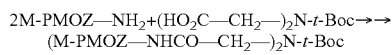

Removal of the t-Boc protecting group by reaction with acid, followed by reaction with succinic anhydride gives the following POZ-2 compound:

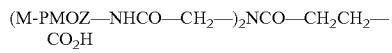  (2)

This POZ-2 carboxylic acid 2 can be directly coupled to target molecules containing amines, or the carboxylic acid can be activated as a succinimidyl ester (or some other active ester) and then coupled with amine-containing target molecules. Alternatively the carboxylic acid can be converted to another functional group which can then be coupled to a target molecule. Examples of "other functional groups" include aldehydes, maleimides, amines, acetylenes, and isothiocyanates. Such methods of conversion are known in the art and are discussed in U.S. Application No. 60/892,212 and Patent Cooperation Treaty Application No. PCT/US2008/002626, each of which are hereby incorporated by reference as if fully set forth herein.

Alternatively, the amine resulting from removal of the t-Boc group above could be reacted with an alkyl 3-bromopropionate followed by hydrolysis of the resulting ester to produce the following compound:

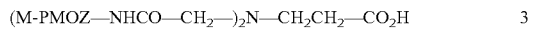  (3)

As can be seen, the branching nitrogen of compound 2 is part of an amide group and thus will not be basic. However, the nitrogen of compound 3 is a tertiary amine and remains basic. As a consequence, compound 3 could be used in an instance in which it is desirable to retain the number of basic groups and positive charges on a hydrolytically stable target molecule-POZ conjugate (target molecule, in this case a protein, represented as PRO—$NH_2$):

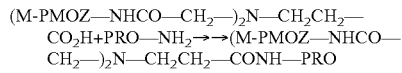

Examining this reaction shows that while the coupling reaction leads to the loss of one basic amine on the protein, a "replacement" basic nitrogen is derived from the branching nitrogen of the POZ-2. This result illustrates one of the novel advantages of the current disclosure. In addition, it can be seen that this chemistry will give a doubling of molecular weight without increasing polydispersity, another novel advantage of the current invention.

Many small molecule branching moieties can be synthesized and used in a similar fashion as above to prepare other POZ-2 compounds. For example, another route to POZ-2 derivatives is to react an electrophilic POZ derivative with a nitrogen-branched compound containing two nucleophilic amine groups. To illustrate, POZ active carbonates can react with nitrogen-branched diamines, or isothiocyanates can react with nitrogen-branched diols:

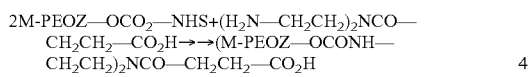  (4)

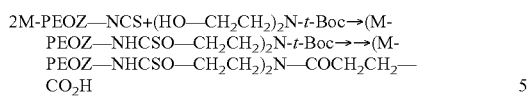  (5)

Another approach to use of the above and related diamines is to trap the diamine with a living POZ cation. Note that polymerization of 2-alkyl-2-oxazolines proceeds through a "living" polymeric cation (FIG. 1), which can be represented as follows (for polymerization of 2-methyl-2-oxazoline initiated with methyl tosylate):

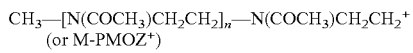

As noted above (FIG. 1), this POZ cation can be "terminated" by reacting with certain nucleophiles. For example, the cation can be terminated or trapped by a diamine to provide a POZ-2:

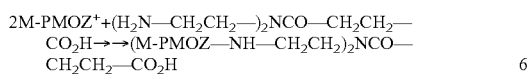  (6)

Note that this reaction produces two secondary, basic amines. These amines can interfere with conversion of the carboxylic acid to an active NHS ester. One approach to avoid this problem is to react the amines with acetic anhydride, in effect extending the POZ by an additional monomer unit.

Yet another route to POZ-2 compounds via trapping of POZ$^+$ is to utilize a single primary amine to trap two POZ$^+$. In the example above, two primary amines attached to a single branch point were used to trap two POZ$^+$. This trapping produces a secondary amine which can react with a second POZ$^+$. The trapping reaction by the secondary amine is significantly slower than with a primary amine, but it can occur if the stoichiometry is correct and sufficient time is allowed. An example of an amine trapping two POZ$^+$ is shown in the following:

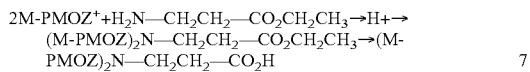  (7)

Table 1 illustrates the various groups in the general structure 1 for the specific POZ-2 compounds described above.

TABLE 1

Various groups in 1 for molecules 2-7. Z = —$CO_2H$ in all cases.

| Cpd. | $R_1$ | $R_2$ | P | A |
|---|---|---|---|---|
| 2 | Me | Me | —$NHCOCH_2$— | —$COCH_2CH_2$— |
| 3 | Me | Me | —$NHCOCH_2$— | —$CH_2CH_2$— |

TABLE 1-continued

Various groups in 1 for molecules 2-7. Z = —CO$_2$H in all cases.

| Cpd. | R$_1$ | R$_2$ | P | A |
|---|---|---|---|---|
| 4 | Me | Et | —OCONHCH$_2$CH$_2$— | —COCH$_2$CH$_2$— |
| 5 | Me | Et | —NHCOSCH$_2$CH$_2$— | —COCH$_2$CH$_2$— |
| 6 | Me | Me | —CH$_2$CH$_2$— | —COCH$_2$CH$_2$— |
| 7 | Me | Me | —(a) | —CH$_2$CH$_2$— |

(a)= Subscript p equals zero.

All the examples of POZ-2 compounds in Table 1 above are carboxylic acids. It is not necessary that this be so. In alternate embodiment, the amine used to make the POZ-2 acids 2 and 3 can also be converted to a range of different reactive groups. To illustrate, reaction of the amine with ethylene oxide would produce an alcohol, and reaction of the amine with maleimidopropionic acid would produce the maleimide. Preparation of POZ-2 carboxylic acid derivatives is advantageous, however, because carboxylic acids are readily purified by ion-exchange chromatography, and they can be converted using well known chemistry to a range of functional groups as discussed above. Conversion to a range of functional groups is desired since this provides a range of chemistries for coupling to the many possible types of target molecules.

Method B—Formation of Nitrogen-Branched POZ-2 Derivatives by Polymerization

A second general route to POZ-2 compounds is to utilize 2-oxazoline polymerization in novel ways. In each of the embodiments below, the POZ-2 derivative may be a monofunctional POZ-2 derivative. Furthermore, each POZ-2 derivative embodiments shown below, the POZ-2 derivatives may form a hydrolytically stable target molecule-POZ-2 conjugate.

For example, direct synthesis of POZ-2 compounds is provided if polymerization is conducted with a difunctional initiator which also contains another functional group such as, but not limited to, alkyl triflate or alkyl tosylate (in the scheme below —OTf represents the —OSO$_2$—CF$_3$ or "triflate" group). Termination is shown with a mercaptide, but other groups such as, but not limited to, morpholine can also be used.

As discussed in the section on minimizing chain transfer, in one embodiment these polymerizations are carried out using at least one of the optimized conditions described there.

A general representation of POZ-2 compounds derived from the use of the difunctional initiators is shown as follows:

$$Z—W—N(Q\text{-}POZ—Nuc)_2 \qquad 9$$

where Q is a linking moiety, including, but not limited to, —(CH$_2$)$_u$—;

W is a second linking moiety, including, but not limited to, —(CH$_2$)$_v$CO—, and —(CH$_2$)$_w$—;

N is a nitrogen atom;

Z is a functional group as described above for a compound of formula 1;

POZ is a polyoxazoline of formula [N(COR$_2$)CH$_2$CH$_2$]$_n$;

Nuc is a nucleophilic terminating agent including, but not limited to, —OH, —SR$_3$, —N(R$_3$)$_2$, piperidinyl (—NC$_5$H$_{10}$), and morpholinyl (—NC$_4$H$_8$O);

R$_2$ is independently selected for each repeating unit of POZ from an unsubstituted or substituted alkyl, alkenyl, alkyl, aralkyl or aryl group;

n is independently selected for each POZ chain from 3 to 1000;

u, v and w are independently 1-10; and

R$_3$ is independently selected for each Nuc group from an alkyl, substituted alkyl, aralkyl, or substituted aralkyl group.

Another polymerization route to POZ-2 derivatives is to react a growing POZ$^+$ with a single molecule of oxazoline having a functional group in the 2-position (2-Z-2-Ox) and then continue polymerization with a 2-alkyl-oxazoline, such as, but not limited to, 2-methyl or 2-ethyl-2-oxazoline. This route is basically the formation of a triblock copolymer in which the middle block consists of a single monomer. To illustrate, initiation of polymerization with methyl triflate of n moles of 2-methyl-2-oxazoline, followed by addition of one unit of the functional oxazoline 2-Z-2-Ox, followed by addition of an additional x moles of 2-methyl-2-oxazoline, fol

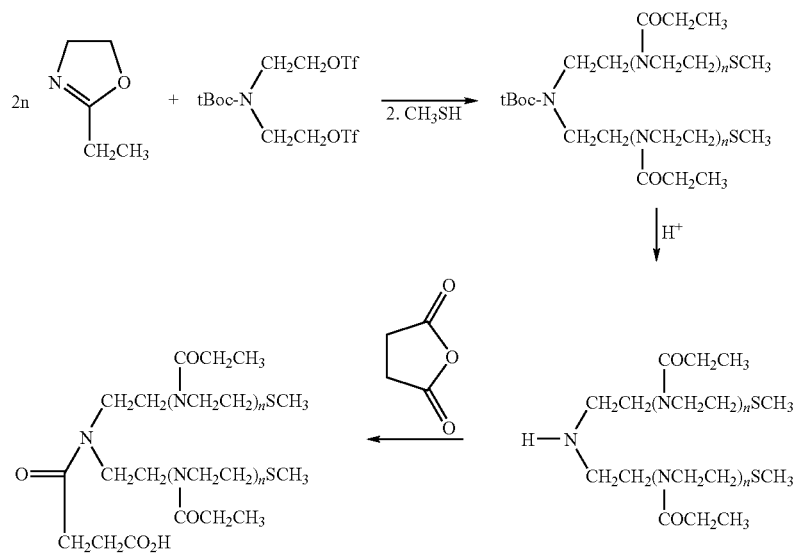

lowed by termination with morpholine, gives the following reaction sequence and the desired product 10:

$$CH_3—OTs+n2\text{-Me-2-Ox}\rightarrow CH_3—[N(COCH_3)CH_2CH_2]_n{}^+CH_3—[N(COCH_3)CH_2CH_2]_n{}^++2\text{-Z-2-Ox}\rightarrow\rightarrow CH_3—[N(COCH_3)CH_2CH_2]_n—N(CO—X)CH_2CH_2{}^+CH_3—[N(COCH_3)CH_2CH_2]_n—N(CO—Z)CH_2CH_2{}^++x2\text{-Me-2-Ox}\rightarrow\rightarrow CH_3—[N(COCH_3)CH_2CH_2]_n—N(CO—Z)CH_2CH_2—[N(COCH_3)CH_2CH_2]_x{}^+CH_3—[N(COCH_3)CH_2CH_2]_n—N(CO—Z)CH_2CH_2—[N(COCH_3)CH_2CH_2]_x{}^++NHC_4H_8O\rightarrow\rightarrow CH_3—[N(COCH_3)CH_2CH_2]_n—N(CO—Z)CH_2CH_2—[N(COCH_3)CH_2CH_2]_x—NC_4H_8O \qquad 10$$

Several different 2-Z-2-oxazolines have been synthesized by several workers including Jordan and colleagues, and one which is of particular interest here is the example in which Z is the propionate ester —$CH_2CH_2CO_2CH_3$. Hydrolysis of the ester would of course give the carboxylic acid. In the work of Jordan, several of these pendant carboxyl groups were introduced per chain. One goal of the present disclosure is to have a single pendant carboxyl group present per polymer chain rather than multiple pendant groups. Adding a single ester-functionalized oxazoline per chain (as shown in the reaction scheme above) will invariably also lead to some chains with no ester-functionalized oxazoline per chain and some chains with two or more. These undesired polymer products can be removed by hydrolysis to the acid followed by ion-exchange chromatography to give the pure POZ-2, which can be readily converted to the NHS active ester, 11:

$$M\text{-PMOZ}—N(COCH_2CH_2C_2NHS)CH_2CH_2\text{-PMOZ}—NC_4H_8O \qquad 11$$

This compound 11 can be coupled to target molecules and it can be further derivatized to give a range of POZ-2 derivatives with differing chemistries.

Compounds derived from this second polymerization route can be represented in general form as follows:

$$R_1—POZ_a—N(CO—U—Z)CH_2CH_2—POZ_b—Nuc \qquad 12$$

where U is a linking moiety as described for Q in the description for a compound of the formula 9;

N is a nitrogen atom;

Z is a functional group as described above for a compound of the formula 1;

$R_1$ is as described above for a compound of the formula 1;

$POZ_a$ is a polyoxazoline of formula —$[N(COR_2)CH_2CH_2]_n$—;

$POZ_b$ is a polyoxazoline of formula —$[N(COR_2)CH_2CH_2]_m$—, $POZ_a$ and $POZ_b$ may be the same or may be different;

$R_1$ is hydrogen, an alkyl, substituted alkyl, aralkyl, or substituted aralkyl group;

$R_2$ is independently selected for each repeating unit of POZ from an unsubstituted or substituted alkyl, alkenyl, alkyl, aralkyl or aryl group;

n and m are each independently selected for each POZ chain from 3 to 1000; and

Nuc is a nucleophilic terminating agent as described above for a compound of the formula 9.

Method C—Formation of POZ-2 Derivatives with Carbon Branch Points

In certain embodiments, the POZ-2 derivatives incorporate a carbon atom or a carbon containing compound as the branching moiety. In each of the embodiments below, the POZ-2 derivative may be a monofunctional POZ-2 derivative. Furthermore, each POZ-2 derivative embodiments shown below, the POZ-2 derivatives may form a hydrolytically stable target molecule-POZ-2 conjugate.

Several synthetic routes may be used to produce such POZ-2 derivatives. For example, POZ active esters or active carbonates can be coupled to the two amino groups of carbon containing compounds, such as, but not limited to, lysine and ornithine. Such POZ-2 derivatives may be represented by the general structure 13 below.

Where $POZ_a$ is a polyoxazoline of formula —$[N(COR_2)CH_2CH_2]_n$—;

$POZ_b$ is a polyoxazoline of formula —$[N(COR_2)CH_2CH_2]_m$—;

$V_I$ is a linking group, including, but not limited to, carbamate (—OCO—NH—) and amide (—CO—NH—);

$V_{II}$ is a linking group, including, but not limited to, carbamate (—OCO—NH—) and amide (—CO—NH—);

$R_1$ is independently selected for each POZ chain from hydrogen, an alkyl, substituted alkyl, aralkyl, or substituted aralkyl group;

$R_2$ is independently selected for each repeating unit of POZ from an unsubstituted or substituted alkyl, alkenyl, alkyl, aralkyl or aryl group;

x is 1 to 20; and n and m are independently selected for each POZ chain from 3 to 1000.

In the structure above, $R_1$, $POZ_a$ and $POZ_b$ may be the same for each of the POZ chains comprising the POZ-2 derivative or may be different. In addition, $V_I$ and $V_{II}$ may be the same for each POZ chain or may be different.

Such an approach utilizing —OCO—NH— as V, x being 4, methyl as $R_1$ and PEOZ as POZ would yield compound 13a.

Such an approach utilizing —CO—NH— as V, x being 4, methyl as $R_1$ and PEOZ as POZ would yield compound 13b.

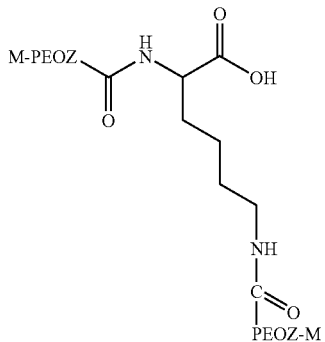

13b

Such an approach utilizing —OCO—NH— as V, x being 3, methyl as $R_1$ and PEOZ as POZ would yield compound 13c.

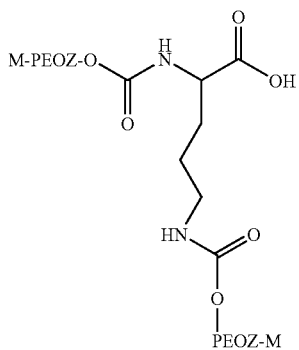

13c

Such an approach utilizing —CO—NH— as V, x being 3, methyl as $R_1$ and PEOZ as POZ would yield compound 13d.

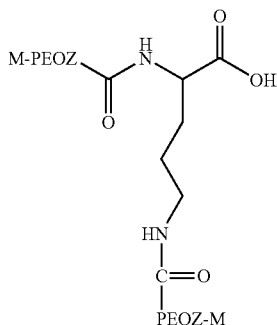

13d

Similarly, one can utilize aromatic rings to link POZ chains to a central branching carbon to form compounds of formula 14.

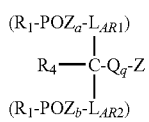

14

Where
$POZ_a$ is a polyoxazoline of formula —[N(COR$_2$)CH$_2$CH$_2$]$_n$—;
$POZ_b$ is a polyoxazoline of formula —[N(COR$_2$)CH$_2$CH$_2$]$_m$—;

Z is a functional group as described above for a compound of the formula 1;
$L_{AR1}$ and $L_{AR2}$ are each linking groups containing a substituted or unsubstituted aryl group,
Q is a linking group including, but not limited to, —(CH$_2$)$_u$— where u is 1-10;
$R_1$ is independently selected for each POZ chain from hydrogen, an alkyl, substituted alkyl, aralkyl, or substituted aralkyl group;
$R_2$ is independently selected for each repeating unit of POZ from an unsubstituted or substituted alkyl, alkenyl, alkyl, aralkyl or aryl group;
$R_4$ is hydrogen, an alkyl, substituted alkyl, aralkyl, or substituted aralkyl group;
n and m are independently selected for each POZ chain from 3 to 1000; and
q is 1 or zero.

In the structure above, $R_1$, POZ, $L_{AR1}$ and $L_{AR2}$ may be the same for each of the POZ chains comprising the POZ-2 derivative or may be different.

As an example of structure 14, thiosalicylate-terminated H-PEOZ may be used to generate compound 15.

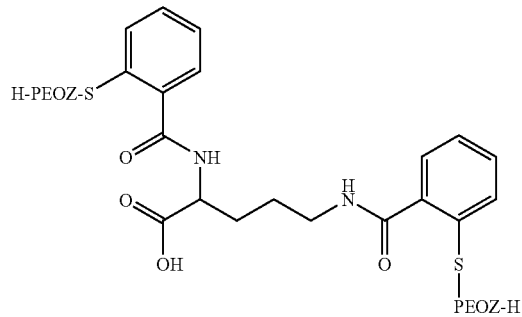

15

In structure 15, $R_4$ is H, $R_2$ is ethyl for each POZ chain, q is zero, Z is —CO$_2$H, and $L_{AR1}$ and $L_{AR2}$ are as shown below:

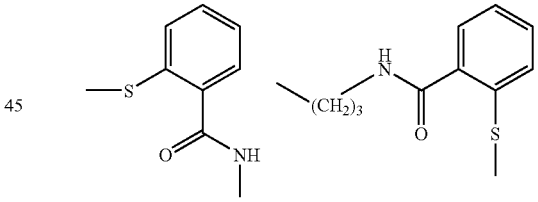

As an additional example of structure 14, thiosalicylate-terminated H-PEOZ may be used to generate compound 15b.

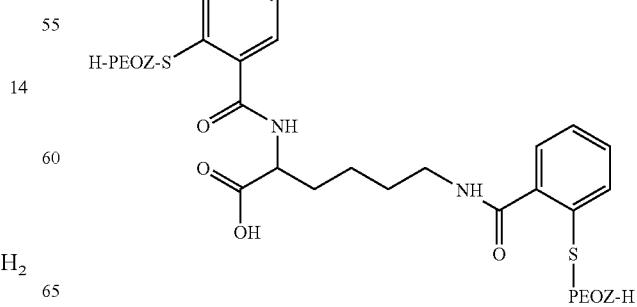

15b

In structure 15b, $R_4$ is H, $R_2$ is ethyl for each POZ chain, q is zero, Z is —$CO_2H$, and $L_{AR1}$ and $L_{AR2}$ are as shown below:

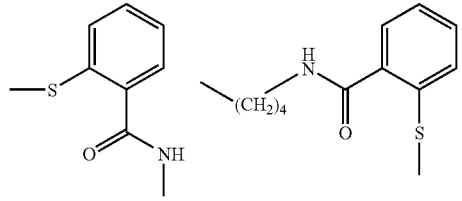

The structures 15 and 15b may be represented generically by the formula below, where x is 1-20, $R_4$ is H and $R_1$, Z, $POZ_a$ and $POZ_b$ are as defined above for compound 14.

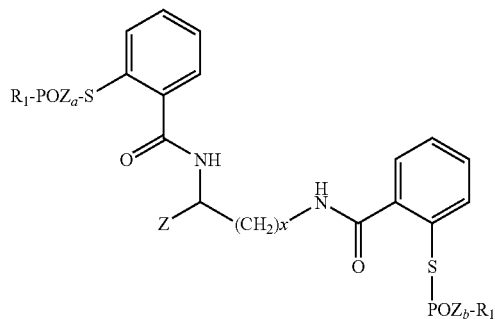

In the above structures 15 and 15b, a linear POZ-thio-salicylate derivative was prepared and used in the described synthesis. This compound is useful as an intermediate in the synthesis of POZ-2 derivatives and as a linear POZ derivative. The structure of the linear POZ-thio-salicylate derivative is shown below as structure 15c.

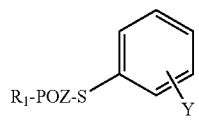

Wherein

POZ is a polyoxazoline of formula —$[N(COR_2)CH_2CH_2]_n$— as described above;

Y is a functional group as described above for Z of a compound of the formula 1; Y is bound to the phenyl ring in a position that is ortho, meta or para to the point of attachment to the S group;

$R_1$ is hydrogen, an alkyl, substituted alkyl, aralkyl, or substituted aralkyl group; and n is from 3 to 1000.

In a specific embodiment, the active group Y as used above is COOH as is in the meta position (illustrated as 15d). However, other Y may be other active groups as described for Z in formula 1 herein. Furthermore, the active group Y may be in the ortho, meta or para positions as indicated in structure 15c.

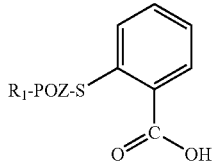

In yet another example of the use of aromatic linkers, one can utilize the aromatic ring as a branching moiety to form compounds of structure 16.

$$(R_1\text{-POZ}—V_v)_2\text{AR-}Q_q\text{-Z} \qquad 16$$

POZ is a polyoxazoline of formula —$[N(COR_2)CH_2CH_2]_n$—;

AR is a branching moiety comprising a substituted or unsubstituted aryl group, wherein AR forms a linkage, either directly or through linking groups, to each POZ chain and the Z group;

Z is a functional group as described above for a compound of the formula 1;

V is a linking group including, but not limited to, carbamate (—OCO—NH—) and amide (—CO—NH—);

Q is a second linking group including, but not limited to, —$(CH_2)_u$ where u is 1-10;

$R_1$ is independently selected for each POZ chain from hydrogen, an alkyl, substituted alkyl, aralkyl, or substituted aralkyl group;

$R_2$ is independently selected for each repeating unit of POZ from an unsubstituted or substituted alkyl, alkenyl, alkyl, aralkyl or aryl group;

q is 1 or zero;

v is independently selected for each POZ chain from 1 or zero; and n is independently selected for each POZ chain from 3 to 1000.

In the structure above, $R_1$, POZ and V may be the same for each of the POZ chains comprising the POZ-2 derivative or may be different.

As an example of structure 16, H-PEOZ active carbonates can be coupled to 3,5-diaminobenzoic acid to give compound 17:

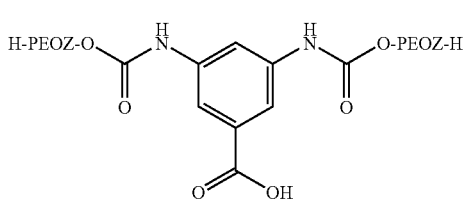

In structure 17, $R_1$ is H, $R_2$ is ethyl, V is —OCO—NH— for each POZ chain, v is 1 for each POZ chain, AR is —$C_6H_3$—, q is zero, and Z is —$CO_2H$.

As another example of structure 16, H-PEOZ active esters may be used to generate compound 17b:

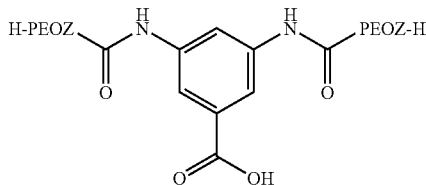

In structure 17b, $R_1$ is H, $R_2$ is ethyl, V is —CO—NH— for each POZ chain, v is 1 for each POZ chain, AR is —$C_6H_3$—, q is zero, and Z is —$CO_2H$.

Use of the POZ-2 Derivatives

The novel monofunctional POZ-2 derivatives prepared as described above are intended for formation of conjugates with various therapeutic and diagnostic molecules. Target molecules of particular interest are protein therapeutics such as, but not limited to, interferons (including alpha, beta and gamma), growth hormone, interleukins, enzymes, antibodies (including antibody fragments and monoclonals), blood factors (including GCSF, erythropoietin, and Factor VIII) and peptides including, but not limited to, insulin. In addition, it is intended that the monofunctional POZ-2 derivatives of the current disclosure be coupled to carbohydrates, oligonucleotides and small-molecule therapeutics In a general embodiment, the present disclosure provides for a hydrolytically stable target molecule-POZ-2 conjugate having the general formula 18:

A-B-TM                18 wherein,
A is a POZ-2 derivative described herein, less any leaving groups eliminated during the reaction of the functional active group on the POZ derivative with a binding partner on the target molecule;
TM is a target molecule; and
B is a linkage formed between the functional active groups of a monofunctional POZ-2 derivative of the present disclosure and a binding partner on the target molecule, it being understood that the nature of the B linkage will depend on the nature of the functional activating group on the monofunctional POZ-2 derivative and the binding partner on the target molecule. Exemplary functional active groups, binding partners and B linkages are provided in Table 2 below. The listing in Table 2 is not meant to be exhaustive and other combinations and resulting B linkages may be envisioned given the teachings of the present disclosure.

TABLE 2

| Functional active group | Binding Partner on target Molecule | B linkage |
|---|---|---|
| Iodoacetamide | SH | Thioether (—S—) |
| Maleimide | SH | Thioether (—S—) |
| Active carbonate | $NH_2$ | Urethane (—NH—CO—O—) |
| Active ester | $NH_2$ | Amide (—NH—CO—) |
| Aldehyde | $NH_2$ | Amine (—NH—) |

EXAMPLES

Reagents were purchased from EM Science or Aldrich and distilled before use. Chlorobenzene and oxazolines were distilled from calcium hydride. GPC was performed on an Agilent Technologies machine with an 1100 quaternary pump and RI detector. Two Phenogel™ GPC columns (Phenomenex, 5μ, 500 A°, 300×7.8 mm) were used in series in a column heater (60° C.). The mobile phase was 100% N,N'-dimethylformamide (DMF) at a flow rate of 1 mL/min. A calibration curve was generated with M-PEOZ—OH samples of different molecular weights as determined by MALDI (750, 1K, 2K, 5K and 10K). MALDI-TOF MS was performed with a Bruker, Microflex™ machine using dithranol as matrix. NMR was performed on a Varian 500 MHz machine.

Example 1

Typical State-of-the-Art Preparation of M-PEOZ—OH 2000

Methyl triflate (0.113 mL, 0.001 mol) was added to a solution of 2-ethyl-2-oxazoline (2.02 mL, 0.020 mol) in acetonitrile (3.0 mL, 6.7M), and the solution stirred for 10 minutes. The reaction was then heated to 80° C. and stirred for 18 hours. Sodium carbonate (1.167 g) and water (1 mL) were added and the resulting mixture was heated overnight at 90° C. After cooling to room temperature, the mixture was diluted with methylene chloride (40 mL) and then decanted into a separatory funnel. Water (5 mL) and brine (3 mL) were added and shaken. The bottom layer was discarded, and the aqueous layer was extracted twice with methylene chloride (2×20 mL). The combined organic layers were dried over magnesium sulfate, filtered and concentrated by rotary evaporation. The crude oil was dissolved in acetone and precipitated by drop-by-drop addition to diethyl ether (80 mL). The resulting powder was dried by vacuum (1.90 g, 94% yield).

GPC showed a single peak with an appreciable high-MW shoulder (Mn=3600 Da, 9%) (FIG. 2A). The main peak had a Mn of 1980 Da, PD 1.1. NMR showed the expected peaks (see Example 6). MALDI-TOF MS gave a set of peaks with a maximum at 2000 Da, PD 1.04 and 99.1 Da separation. The MALDI spectrum also showed a second set of peaks with 99.1 Da separation, but with each peak 14 Da less than the main set. The maximum for this set of peaks occurred at 1600 Da.

Example 2

Second State-of-the-Art Preparation of M-PEOZ—OH 2000

Chlorobenzene (6.9 mL), acetonitrile (2.3 mL) and methyl triflate (0.164 mL, 1.5 mmole) were mixed at ambient temperature under nitrogen. 2-Ethyl-2-oxazoline (3.05 mL, 3.0 g, 30 mmole) was then added slowing with stirring. The mixture was heated to 70° C. and stirred for 8 hours. The reaction mixture was then cooled to room temperature by immersion in an ice bath. Potassium hydroxide (2 mmol) in 1 mL of methanol was added and the mixture stirred for one hour. The mixture was then extracted with methylene chloride (40 mL). The methylene chloride layer was separated and washed three times with water (40 mL total). The organic layer was dried, filtered and concentrated by rotary evaporation to 5 mL. The product was precipitated by addition to diethyl ether (100 mL) and dried under vacuum (yield 0.7 g).

Figure 2B:
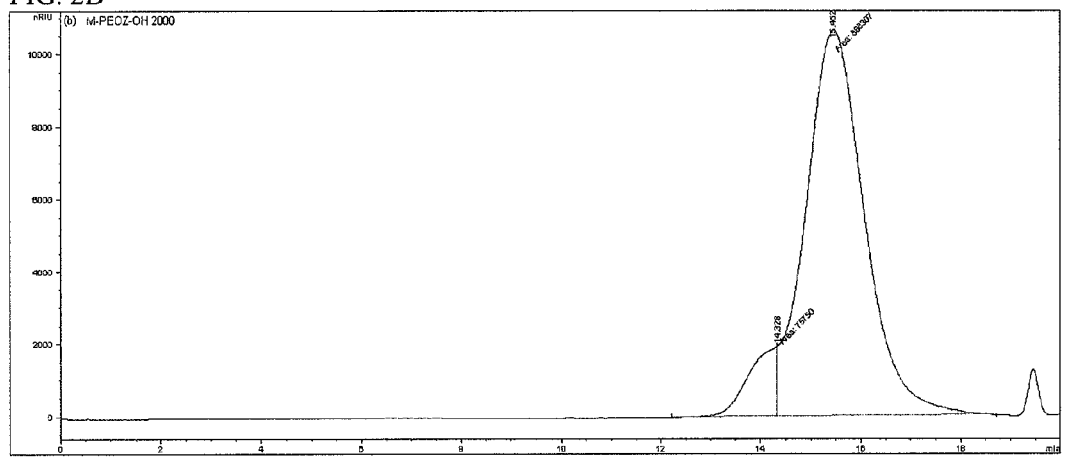

GPC showed a single peak with an appreciable high-MW shoulder (Mn=3300 Da, 6%) (FIG. 2B). The main peak had a Mn of 2200 Da, PD 1.07. NMR showed the expected peaks (see Example 6). MALDI-TOF MS gave a set of peaks with a maximum at 2300 Da, and 99.1 Da separation. The MALDI spectrum also showed a second set of peaks with 99.1 Da separation, but with each peak 14 Da less than the main set. The maximum for this set of peaks occurred at 2100 Da.

Example 3

Effect of Ethyldiisopropylamine on M-PEOZ⁺Termination

Methyl triflate (0.0566 mL, 0.5 mmol) was added to a solution of 2-ethyl-2-oxazoline (1.01 mL, 10.0 mmol) in chlorobenzene (5 mL, 2M) at room temperature, and the solution stirred for 10 minutes. The solution was then heated to 110° C. and stirred for 30 minutes. The solution was cooled to 0° C. and diisopropylethylamine (0.261 mL, 1.5 mmol) was added and the resulting mixture was stirred for 18 hours at 50° C. The mixture was cooled to room temperature and added drop-by-drop into diethyl ether (50 mL) to give a white precipitate. The solid was dried under vacuum in almost quantitative yield.

GPC showed two peaks, one at approximately 2000 Da (24%) and one at approximately 3800 Da (76%). The MALDI spectrum confirmed the presence of both high- and low-MW products.

Example 4

Effect of 2,6-Lutidine on M-PEOZ$^+$ Termination

Methyl triflate (0.0424 mL, 0.375 mmol) was added to a solution of 2-ethyl-2-oxazoline (0.758 mL, 7.5 mmol) in chlorobenzene (3.75 mL) at room temperature, and the solution stirred for 10 minutes. The solution was then heated to 110° C. and stirred for 30 minutes. The solution was cooled to 0° C. and 2,6-lutidine (0.170 mL, 1.5 mmol) was added and the resulting mixture was stirred for 18 hours at 50° C. The mixture was cooled to room temperature and added drop-by-drop into diethylether (20 mL) to give a white precipitate. The solid was dried under vacuum in almost quantitative yield.

GPC showed two peaks, one at approximately 2000 Da (89%) and one at approximately 4000 Da (11%) consistent with some dimerization. The NMR spectrum showed peaks at 4.2 and 5.0 ppm, consistent with the presence of unterminated oxazolinium cation.

Example 5

Termination of Oxazoline Polymerization with Methyl Glycolate

Methyl triflate (0.453 mL, 0.004 mol) was added to a solution of 2-ethyl-2-oxazoline (4.04 mL, 0.040 mol) in chlorobenzene (5 mL, 2M) at room temperature, and the solution stirred for 10 minutes. The solution was then heated to 110° C. and stirred for 30 minutes. The solution was cooled to 0° C. and 2,6-lutidine (0.929 mL, 0.008 mol) and methyl glycolate (0.609 mL, 0.008 mol) were added and the resulting mixture was stirred for 18 hours at room temperature. The mixture was cooled to room temperature and added drop-by-drop into diethyl ether (1500 mL) to give a white precipitate. The solid was dried under vacuum in almost quantitative yield.

The NMR showed peaks at 4.46 and 4.99 ppm, consistent with oxazolinium ion and consistent with failure of the glycolate to terminate polymerization.

Example 6

Preparation of M-PEOZ—OH 2000 Under Optimal Conditions

Chlorobenzene (30 mL) and MeOTf (344 μL, 3.0 mmol) were mixed at room temperature under nitrogen and added to 2-Et-2-Ox (6.06 mL, 60 mmol) in 20 mL of chlorobenzene. The mixture was stirred for 35 minutes with heating to 110° C. The mixture was next cooled to 0 C and then a solution of sodium carbonate (2.12 g) in 40 mL of water was added and stirred overnight. The mixture was poured into a separatory funnel and 40 mL of water was added. The bottom layer was removed and the aqueous layer was extracted with methylene chloride (3×60 mL). The combined organic layers were dried over magnesium sulfate, filtered and concentrated by rotary evaporation. The thick oily residue as dissolved in 7 mL methylene chloride and added drop-by-drop to diethyl ether (80 mL) at 0° C. This precipitation was repeated to provide 4.2 g of a white powder (84% yield).

NMR (Varian, 500 MHz, 10 mg/mL CDCl$_3$) shows the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OH) appears at 3.8 ppm (s). GPC showed a single peak, with no high MW shoulder and no appreciable tailing; Mn=1900 Da, and polydispersity (PD)=1.03 (FIG. 3A). MALDI gave a spectrum with Mn=1900 Da, and 99.1 Da mass units of separation. The calculated PD was 1.03.

p-Nitrophenyl Carbonate derivatization. The product was converted into the p-nitrophenyl carbonate, which was then purified and hydrolyzed in the presence of 0.2N NaOH solution (pH 8). Measurement of the p-nitrophenol (UV absorption at 400 nm, ε=18,000 M$^{-1}$ cm$^{-1}$) gave degree of —OH substitution as 99%.

Example 7

Preparation of M-PEOZ—OH 5000 Under Optimal Conditions

Chlorobenzene (80 mL) and MeOTf (354 μL, 3.2 mmole) were mixed at room temperature under nitrogen in a one-necked 250 mL round bottom flask. 2-Et-2-Ox (16.4 mL, 16.0 g, 160 mmol) was added slowly into the flask with stirring. The mixture became cloudy upon addition of oxazoline. The mixture was heated at 42° C. and stirred for one h. As the mixture warmed it became clear. The mixture was then heated to 80° C. and stirred for 3.75 h. The mixture was next cooled to room temperature by immersing in an ice bath for 15 min.

The polymerization was terminated by the addition of 40 mL of water and 2 g of sodium carbonate, followed by stirring for 30 mins. The aqueous layer was separated and the organic layer was once again extracted with 40 mL of water and 1 g of sodium carbonate followed by stirring for 30 mins. The aqueous layer was separated and combined with the first aqueous layer, and the combined aqueous solution was stirred overnight at room temperature. The cloudy aqueous layer (~80 mL) was then acidified with 0.5 M HCl (~40 mL) until the pH was less than 6 (pH paper) and a clear solution was obtained.

The polymer was then extracted 4 times with methylene chloride (200 mL each time) and the combined organic layers were dried with anhydrous magnesium sulfate for one hour with stirring. The methylene chloride solution was evaporated under vacuum, and the resulting residue was dissolved into 25 mL of dry methylene chloride and precipitated by drop-by-drop addition to 250 mL ethyl ether (room temperature). The resulting white solid was then dried overnight in a vacuum oven at 50° C. The dried material was a white powder (14.1 g, 88% yield).

NMR (Varian, 500 MHz, 10 mg/mL CDCl$_3$) shows the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OH) appears at 3.8 ppm (s). GPC GPC showed a single peak with retention time of 13.5 min. Mn=4100 Da, and polydispersity (PD)=1.06. Mn (theoretical)=4980 Da. A small shoulder at 12.4 min indicates a high MW impurity of about 1%; Mn=8900 Da (FIG. 3B). MALDI gave a spectrum with Mn=4910 Da, and 99.1 Da mass units of separation. The PD was 1.02. p-Nitrophenyl Carbonate derivatization. The product was converted into the p-nitrophenyl carbonate, which was then purified and hydrolyzed in the presence of 0.2N NaOH solution (pH 8). Measurement of the p-nitrophenol (UV absorption at 400 nm, ε=18,0001 M$^{-1}$ cm$^{-1}$) gave degree of —OH substitution as 99%.

Example 8

Synthesis of POZ p-Nitrophenyl Carbonate

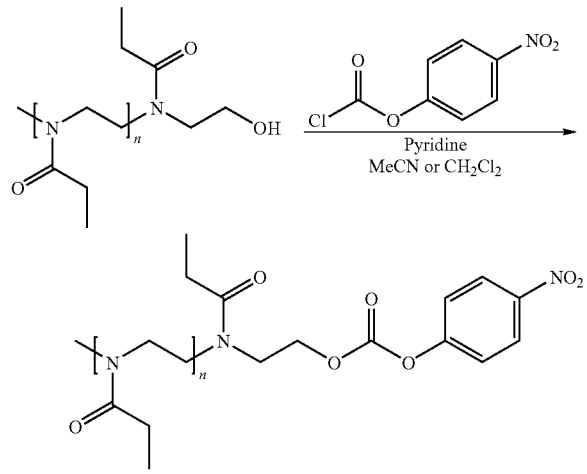

A solution of M-PEOZ—OH (10.0 g, 1.0 mmol) in 80 mL of acetonitrile was concentrated using rotary evaporation. The residue was dissolved in methylene chloride (40 mL) and p-nitrophenylchloroformate (1.61 g, 7.96 mmol) was added at 0° C. Pyridine (0.80 mL, 9.95 mmol) was added, drop by drop, and the mixture stirred at room temperature for three hours. The mixture was concentrated using rotary evaporation and then added to diethyl ether to give a white precipitate. Solvent was decanted and the precipitate was dried under vacuum. The product was dissolved in slightly acidic water, stirred for 20 minutes and filtered. The product was extracted in methylene chloride and dried over magnesium sulfate. The solution was concentrated by rotary evaporation and precipitated by addition to diethyl ether. The solvent was decanted and the product dried under vacuum. Yield 8.7 g. NMR (Varian, 500 MHz, 10 mg/mL CDCl$_3$) shows the usual backbone peaks at 1.12 ppm (s, 3H, CH$_3$CH$_2$CO—); 2.31 ppm (small m) and 2.41 ppm (large s) (total area 2H, CH$_3$CH$_2$CO—); 3.47 ppm (s, 4H, —NCH$_2$CH$_2$N—); 7.38 ppm (d, 2H, J=5.2 Hz); and 8.29 ppm (d, 2H, J=5.2 Hz). The initiating methyl peak appears as two singlets at 2.9 ppm (small) and 3.03 ppm (large) (CH$_3$—NCH$_2$CH$_2$). The terminal methylene (—CH$_2$—O—CO—) appears at 4.42 ppm (s). p-Nitrophenyl Carbonate substitution. The product was hydrolyzed in the presence of 0.2N NaOH solution. Measurement of the free p-nitrophenol (UV absorption at 400 nm, ε=17,000 M$^{-1}$ cm$^{-1}$) gave degree of —OH substitution of 100%.

Example 9

Synthesis of POZ Amine

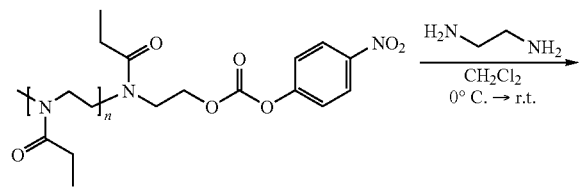

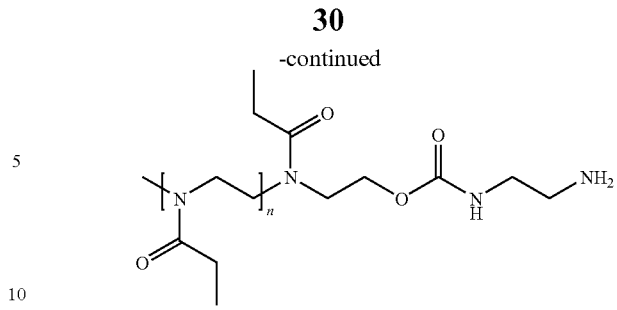

A solution of M-PEOZ-PNPC (3.60 g, 0.694 mmol) in methylene chloride (20 mL) was cooled to 0° C. and ethylene diamine (2.33 mL, 34.7 mmol) was added. The solution was stirred for one hour in the cold and then 18 hours at room temperature. The mixture was concentrated using rotary evaporation, diluted by addition of n-butyl alcohol (20 mL) and the alcohol then removed by rotary evaporation (to remove the diamine azeotropically). The residue was dissolved in methylene chloride and added to diethyl ether. The solvent was decanted and the white powder dissolved in methylene chloride (100 mL). The solution was washed with 1N NaOH solution. The aqueous phase was washed twice with methylene chloride (2×70 mL), and the organic layers combined and dried over magnesium sulfate. The solution was filtered, concentrated and added to ethyl ether. The solvent was decanted and the white powder dried under vacuum.

NMR (Varian, 500 MHz, 10 mg/mL CDCl$_3$) shows the usual backbone peaks at 1.12 ppm (s, 3H, CH$_3$CH$_2$CO—), 2.31 ppm (small s) and 2.41 ppm (large s) (total area 2H, CH$_3$CH$_2$CO—), and 3.47 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OCO—NH—) appears at 4.2 ppm (br s, 2H) and the protons associated with ethylene diamine appear at 2.82 ppm (m, 2H, —NH—CH$_2$—CH$_2$—NH$_2$) and 3.23 ppm (m, 2H, —NH—CH$_2$—CH$_2$—NH$_2$).

Example 10

Synthesis of POZ Succinimidyl Carbonate

A solution of M-PEOZ—OH (0.5 g, 0.23 mmol) was prepared in 5 mL of dry dichloromethane or dry acetonitrile and concentrated by rotary evaporation. A suspension was prepared of disuccinimidyl carbonate (0.24 g, 0.9 mmol) in 5 mL of dry dichloromethane or dry acetonitrile. Pyridine (0.094 mL, 1.16 mmol) was added to this suspension. The M-PEOZ—OH solution was added to the above suspension, drop by drop, and the mixture was stirred overnight at room temperature. The mixture was filtered, concentrated using rotary evaporation, and then added to diethyl ether. The solvent was decanted and the white powder dried under vacuum. The powder was dissolved in dry acetone and precipitated by addition to diethyl ether. Yield 0.6 g. NMR (Varian, 500 MHz, 10 mg/mL CDCl$_3$) shows the usual backbone peaks at 1.12 ppm (s, 3H, CH$_3$CH$_2$CO—); 2.31 ppm (small m) and 2.41 ppm (large s) (total area 2H, CH$_3$CH$_2$CO—); 3.47 ppm (s, 4H, —NCH$_2$CH$_2$N—); 2.70 ppm (s, 4H, SC group). The initiating methyl peak appears as two singlets at 2.9 ppm (small) and 3.03 ppm (large) (CH$_3$—NCH$_2$CH$_2$). The terminal methylene (—CH$_2$—O—CO—) appears at 4.24 ppm (s).

Example 11

Synthesis of POZ—COOH a. Synthesis of Methyl Ester

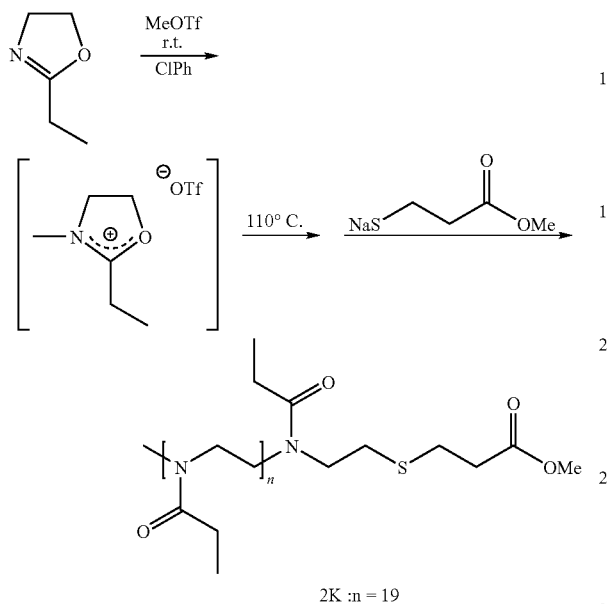

A solution of 1 mmol of M-PEOZ+ was prepared in chlorobenzene as described above. The solution was cooled to room temperature. Methyl 3-mercaptopropionate (0.65 mL, 6 mmol) was added drop by drop to a suspension of NaH (0.12 g, 5 mmol) in THF at 0° C. The M-PEOZ+ solution was then added slowly to the THF solution. The resulting mixture was warmed to room temperature and stirred overnight. The reaction mixture was filtered and added to ether to get a white precipitate. The solvent was decanted and the solid dried under vacuum to give 1.5 g of a white powder.

NMR (Varian, 500 MHz, 10 mg/mL CDCl$_3$) shows the usual backbone peaks at 1.12 ppm (s, 3H, CH$_3$CH$_2$CO—); 2.31 ppm (small m) and 2.41 ppm (large s) (total area 2H, CH$_3$CH$_2$CO—); 3.47 ppm (s, 4H, —NCH$_2$CH$_2$N—). The initiating methyl peak appears as two singlets at 2.9 ppm (small) and 3.03 ppm (large) (CH$_3$—NCH$_2$CH$_2$). The terminal methylene (—CH$_2$—COO—CH$_3$) appears at 2.64 ppm (s), its neighboring methylene (S—CH$_2$—CH$_2$—CO—) appears at 2.81 ppm (s) and the methylene adjacent to the sulfur group (—CH$_2$—S—CH$_2$—) appears at 2.71 ppm (s). The methyl ester group (—CH$_2$—COO—CH$_3$) appears as a sharp singlet at 3.71 ppm.

b. Synthesis of Thioacid

A solution of ester from above (8.1 g, 0.004 mol) in 20 mL methanol was prepared and mixed with 30 mL of a 0.05N NaOH solution (0.02 mol). The mixture was stirred at room temperature for 40 min and then acidified with 5% HCl. The methanol was removed by rotary evaporation and the solution extracted with dichloromethane. The extract was dried over magnesium sulfate, filtered, concentrated, and precipitated by addition to ether. The ether was decanted and the residue dried under vacuum. The NMR spectrum showed the disappearance of the methyl ester peak at 3.71 ppm. GPC showed a high MW shoulder of 6%. The main peak gave Mn 1870 Da, PD of 1.15. The above sample was purified by ion-exchange chromatography using a DEAE Sepharose FF medium. GPC of the product gave a single main peak with no high-MW shoulder, with Mn 1970 Da and PD 1.08. MALDI gave Mn 2090 Da and PD of 1.04.

Example 12

Synthesis of POZ-2 Compound 1 a. Coupling of Bis-Acid with POZ—NH$_2$

A solution of Boc-N(CH$_2$CO$_2$H)$_2$ (0.116 g, 0.498 mmol) and hydroxybenztriazole (0.337 g, 2.49 mmol) in acetonitrile (50 mL) was concentrated using rotary evaporation to remove water. The residue was dissolved in methylene chloride (20 mL) and a solution of dicyclohexylcarbodiimide (0.308 g, 1.49 mmol) in methylene chloride (20 mL) was added. After the mixture had stirred for 3 hours at room temperature mPEOZ—NH$_2$ 2100 (2.46 g, 1.20 mmol) was added and the flask neck was rinsed with methylene chloride (10 mL). The mixture was stirred for 20 hours at room temperature, filtered, concentrated to 10 mL, and dripped into diethyl ether (80 mL) to give a white precipitate. The supernatant was decanted, and the solid was dried under vacuum to give 2.36 g of white powder.

NMR (Varian, 500 MHz, 10 mg/mL CDCl$_3$) shows the usual backbone peaks at 1.12 ppm (s, 3H, CH$_3$CH$_2$CO—); 2.31 ppm (small s) and 2.41 ppm (large s) (total area 2H, CH$_3$CH$_2$CO—); and 3.48 ppm (s, 4H, —NCH$_2$CH$_2$N—). The initiating methyl peak appears as two singlets at 2.9 ppm (small) and 3.05 ppm (large) (CH$_3$—NCH$_2$CH$_2$). The terminal methylene (—CH$_2$—OCO—NH—) appears at 4.2 ppm (br s, 4H) and the protons associated with the Boc-diacid appear at 3.87 ppm (d, 4H, —N—(CH$_2$CO$_2$H)$_2$). The t-boc group had a peak at 1.41 ppm (s, 9H). GPC showed two peaks, one at Mn 4300 Da (90%, PD=1.02) and a second at 2100 Da (10%). MALDI gave a spectrum with two peaks at Mn 4400 Da (PD=1.02) and 2200 Da, and 99.1 mass units of separation.

b. Removal of t-Boc Group

The above produce (1.28 g) was added to a 4M solution of hydrochloric acid in dioxane (10 mL) cooled in an ice bath. The mixture was stirred at room temperature for 40 min. The mixture was concentrated by rotary evaporation, neutralized with saturated aqueous sodium bicarbonate and extracted three times with dichloromethane. The organic solution was dried over magnesium sulfate, filtered, concentrated and added to diethyl ether. The solution was decanted and the white powder dried under vacuum. Yield 1.15 g. NMR showed that the t-boc group had been removed.

Example 13

Synthesis of H-PEOZ Thio-Salicylic Acid

A solution of 2-ethyl-2-oxazoline (10.0 mL, 9.82 g, 99.1 mmol) and chlorobenzene (25 mL) were mixed at ambient temperature under argon in a 100 mL round-bottom flask. Triflic acid (69.5 µL, 0.785 mmol) was then pipetted into the flask and mixed with stirring. The reaction mixture was stirred for 5 hours at 85° C. At the end of the polymerization reaction, the mixture was cooled down in an ice bath.

In a separate 250 mL flask, NaH (60% dispersion in mineral oil, 157 mg, 3.92 mmol) and chlorobenzene (50 mL) were mixed, and methyl thiosalicylate (1.1 mL, 7.86 mmol) was slowly injected into this mixture. The light yellowish cloudy solution was stirred under argon at room temperature for 4 hours.

The living polymer solution was transferred with the aid of a cannula into the termination mixture (methyl thiosalicylate/NaH), and the solution was stirred under argon overnight at room temperature, and then for 48 hours at 40° C.

Deionized water (100 mL) was added to the reaction mixture. The chlorobenzene in the mixture was removed at 29° C. and 34 mbar using a rotary evaporator. The pH of the remaining aqueous solution was adjusted to 12.3 by addition of 0.5 N NaOH, and the solution was stirred for 6 hours at room temperature constantly maintaining the solution pH at 12.0-

12.5. The solution pH was adjusted to 3.0 by 1.0 N HCl, and the solution was washed with ethyl ether (3×300 mL). The pH of the aqueous solution was adjusted to 5.3, followed by extraction with dichloromethane (2×300 mL). The DCM solution was dried over anhydrous $Na_2SO_4$, filtered, and the filtrate was concentrated. The solution was then precipitated by addition to 800 mL of ethyl ether. The precipitate was filtered, and dried under high vacuum. Yield: 7.3 gm. The percent formation of the desired H-PEOZ-T-Salicylic Acid was determined by anion exchange chromatography (DEAE) as 44%. The peak molecular weight of the polymer was 12,200 Da as determined by GPC. Gel filtration chromatography indicated the crude product contained 47% of H-PEOZ-T-salicylic acid.

The crude product (6.7 gm) was purified by anion exchange chromatography (DEAE Sepharose FF), to give 2.0 gm of pure H-PEOZ-T-Salicylic acid. GPC analysis showed Mn 14,700 Da, Mp=13,300 Da, PDI=1.10. GFC showed that the product was 100% pure.

$^1$H NMR (Varian 500 MHz, $CDCl_3$, δ) shows the usual polymer backbone peaks at 1.12 ppm (s, 3H, $CH_3CH_2CO$—); 2.31 ppm (small m) and 2.41 ppm (large s) (total area 2H, $CH_3CH_2CO$—); 3.47 ppm (s, 4H, —$NCH_2CH_2N$—); terminal methylene attached to the S atom at 3.13 ppm (m, 2H, —$NCH_2CH_2$—S—Ar), and for the four aromatic protons of the salicylate molecule: 8.00 ppm (m, 1H, Ar) and 7.10-7.70 ppm (m, 3H, Ar).

Example 14

Synthesis of M-PEOZ$_2$-Lysine-Ethyl Ester

Synthesis of (M-PEOZ)$_2$-Lysine Ethyl Ester—Route 1

To a solution of mPEOZ thio-acetic acid NHS ester (Mn=5080 Da, 1.00 g, 0.197 mmol) in methylene chloride (10 mL) were added lysine ethyl ester dihydrochloride (0.0222 g, 0.0896 mmol) and DMAP (0.0548 g, 0.448 mmol). After stirring for 18 hours at room temperature, the mixture was dripped into diethyl ether (80 mL) to give a white precipitate. The solution was decanted and then the remaining white powder was stirred in diethyl ether for 10 minutes. The resulting mixture was poured into a fritted glass filter and dried under vacuum to give the desired product. GPC and GFC showed a mixture of 10k and 5k species with a ratio of 85% and 15%.

Synthesis of (M-PEOZ)$_2$-Lysine ethyl ester—Route 2

A solution of mPEOZ-thio-acetic acid (M-PEOZ—S—$CH_2$—$CIO_2$—NHS) (Mn=4980 Da, 1.50 g, 0.302 mmol, 2.1 eq.) and 1-HOBT (0.0971 g, 0.719 mmol, 5 eq.) in acetonitrile (60 mL) was concentrated using rotary evaporation. The residue was dissolved in dry $CH_2Cl_2$ (15 mL) and then DCC (0.0899 g, 0.431 mmol, 3 eq.) was added. After the mixture was stirred for 3 hours at room temperature, L-lysine ethyl ester dihydrochloride (0.0355 g, 0.144 mmol, 1 eq.) and DMAP (0.0527 g, 0.431 mmol, 3 eq.) were added as a solid. After stirring for 18 hours at room temperature, the mixture was stirred for an additional 24 hours and filtered into ether (80 mL) to give a white precipitate. After the solution was decanted, diethyl ether was added into the remaining white powder and stirred for 5 minutes. The resulting mixture was filtered and dried under vacuum to give 1.35 g of the targeted PEOZ2-Lysine-ethyl ester as a white powder in 94% yield. NMR (Varian, 500 MHz, 10 mg/mL $CDCl_3$) shows the peaks for the lysine core, and the usual backbone peaks, at 1.28 ppm (t, 3H, $CH_3CH_2O$—); 1.58 ppm (m, 2H, —C(=O)$NHCH_2CH_2CH_2$—); 1.69 ppm (m, 2H, —C(=O)$NHCH_2CH_2$—); 1.92 ppm (m, 2H, —$CH_2CH(CO_2H)$NH—); 4.17 ppm (m, 2H, $CH_3CH_2O$—); and 4.52 ppm (m, 1H, —$CH_2CH(CO_2H)NH$—). GPC showed the mixture of three components: a higher molecular weight shoulder (Mn=17700 Da, PD=1.18, 8.6%), main product (Mn=10000 Da, PD=1.03, 78.5%), and lower molecular weight impurity (Mn 4815 Da, PD1.04, 12.9%).

Prophetic Examples

Example 15

Synthesis of (H-PEOZ-Salicylate)$_2$-Lysine Carboxylic Acid 30K

H-PEOZ-Thio-Salicylic Acid 15K from above (872 mg, 0.0593 mmol, 1.0 equiv.) and hydroxybenztriazole (19.1 mg, 0.1412 mmol, 2.38 equiv.) were dissolved in 40 mL acetonitrile. The solution was evaporated to dryness by rotary evaporation. Anhydrous dichloromethane (10 mL) was added to dissolve the residue, followed by the addition of dicyclohexylcarbodiimdie (DCC-17.7 mg, 0.0848 mmol, 1.43 equiv.) was added into the solution. The solution was stirred for three hours at room temperature under argon. L-Lysine ethyl ester dihydrochloride (6.78 mg, 0.02609 mmol, 0.44 equiv.) was added into the solution, followed by the addition of dimethylaminopyridine (DMAP—17.3 mg, 0.141 mmol, 2.38 equiv.). The solution was allowed to stir overnight at room temperature under argon.

The reaction mixture was concentrated by rotary evaporation, and was then precipitated by addition into 100 mL of diethyl ether. The precipitate was filtered, and then dried under vacuum. Yield: 0.7 gm. Molecular weight was verified by GPC.

The crude product was purified by anion exchange chromatography to remove unreacted H-PEOZ-T-Salicylic Acid. The purified product was hydrolyzed at pH 12, to give the desired POZ-2 carboxylic acid. This method may also be used to couple POZ chains to ornithine.

Example 16

Synthesis of H-PEOZ-2 Benzoic Acid 20K 3,5-Diaminobenzoic acid (4.3 mg, 0.028 mmol, 0.40 equiv.) was dissolved in 10 mL of anhydrous DMF. To the solution was added H-PEOZ-p-NPC 10K (1.00 gm, 0.0692 mmol, 1.0 equiv.; an active NHS ester can also be used), followed by addition of N,N-Diisopropylethyl amine (DIPEA, 36.2 µL, 0.208 mmol, 3.0 equiv.). Following overnight stirring at room temperature, the solution was evaporated to dryness by rotary evaporation under vacuum at 50° C. The residue was dissolved in dichloromethane, and then precipitated by addition into diethyl ether with stirring. The precipitate was filtered and dried under vacuum. The molecular weight of H-PEOZ2-benzoic acid was verified by GPC.

Example 17

Succinoylation of Bis-M-PEOZ Derivative from Example 11.c

The product from above (0.0001 moles), succinic anhydride (0.0003 moles), DMAP (0.0002 moles), and triethylamine (0.0002 moles) are dissolved in dry dioxane (20 ml) and stirred for 24 hours at room temperature. The solvent is removed under vacuum and the residue dissolved in 10 ml of methylene chloride. The product is precipitated in 100 ml of ether and the precipitate recovered by decanting the solvent. The residue is treated with 20 ml of 1N HCl and then extracted with 3×20 ml portions of $CH_2Cl_2$. The combined extracts are dried over $Na_2SO_4$ and the product carboxylic acid obtained by evaporation of the solvent.

Example 18

Coupling of Bis-Amine with M-PEOZ—OCO₂—NHS. Compound 3

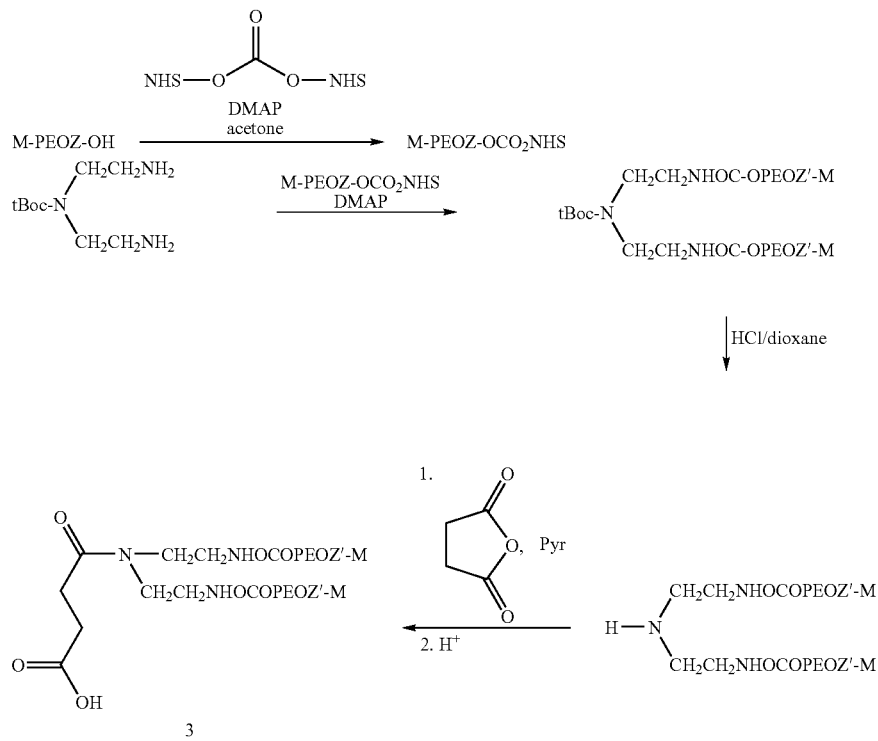

To 0.01 moles of M-PEOZ—OCO₂NHS in 25 ml of methylene chloride is added 0.005 moles of N-t-Boc bis-aminoethylimine, 0.01 moles of DCC and 0.01 moles of DMAP and the mixture stirred at room temperature for 6 h. The mixture is concentrated to 10 ml and poured into 100 ml of ethyl ether. The precipitate is collected by decanting the solvent and drying the residue under vacuum at 40° C.

b. Removal of t-boc

The t-boc group is removed from the product by stirring with hydrochloric acid as described above.

c. Succinoylation of Bis-M-PEOZ Derivative

The product from above (0.0001 moles), succinic anhydride (0.0003 moles), DMAP (0.0002 moles), and triethylamine (0.0002 moles) are dissolved in dry dioxane (20 ml) and stirred for 24 hours at room temperature. The solvent is removed under vacuum and the residue dissolved in 10 ml of methylene chloride. The product is precipitated in 100 ml of ether and the precipitate recovered by decanting the solvent. The residue is treated with 20 ml of 1N HCl and then extracted with 3×20 ml portions of $CH_2Cl_2$. The combined extracts are dried over $Na_2SO_4$ and the product carboxylic acid obtained by evaporation of the solvent.

Example 19

Polymerization Using Bis-Triflate. Synthesis of Compound 9

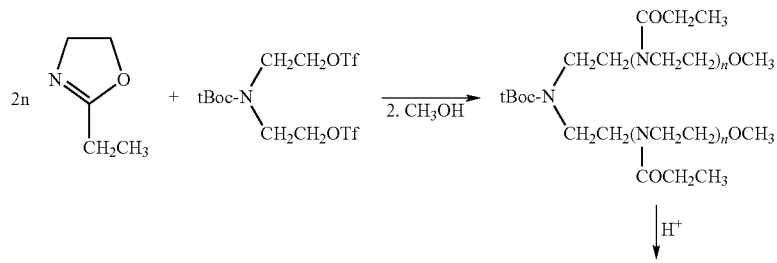

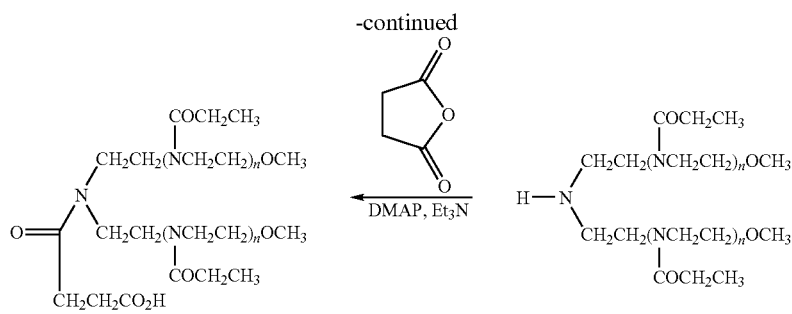

a. Polymerization with t-Boc Bis-Ethyl Triflate

To 0.02 moles (2.0 g) of 2-ethyl-2-oxazoline in 20 ml of dry chlorobenzene is added 0.001 moles (g) of t-Boc bis-ethyl triflate at 0° C. The mixture is heated rapidly with stirring to 80° C. and held at that temperature for 5 h. The solvent is evaporated and 10 ml of methanol and 50 mg of sodium methoxide were added. After stirring 5 h, the mixture is filtered and poured into 100 ml of ether. The precipitate is collected by decanting the ether and vacuum drying the residue.

b. Removal of t-boc

The t-boc group is removed from the product by treatment with hydrochloric acid, as described above.

c. Succinoylation of Bis-M-PEOZ Derivative

The product from above (0.0001 moles), succinic anhydride (0.0003 moles), DMAP (0.0002 moles), and triethylamine (0.0002 moles) are dissolved in dry dioxane (20 ml) and stirred for 24 hours at room temperature. The solvent is removed under vacuum and the residue dissolved in 10 ml of methylene chloride. The product is precipitated in 100 ml of ether and the precipitate recovered by decanting the solvent. The residue is treated with 20 ml of 1N HCl and then extracted with 3×20 ml portions of $CH_2Cl_2$. The combined extracts are dried over $Na_2SO_4$ and the product carboxylic acid obtained by evaporation of the solvent.

Example 20

Introduction of Branching Moiety During Polymerization Process. Compound 8

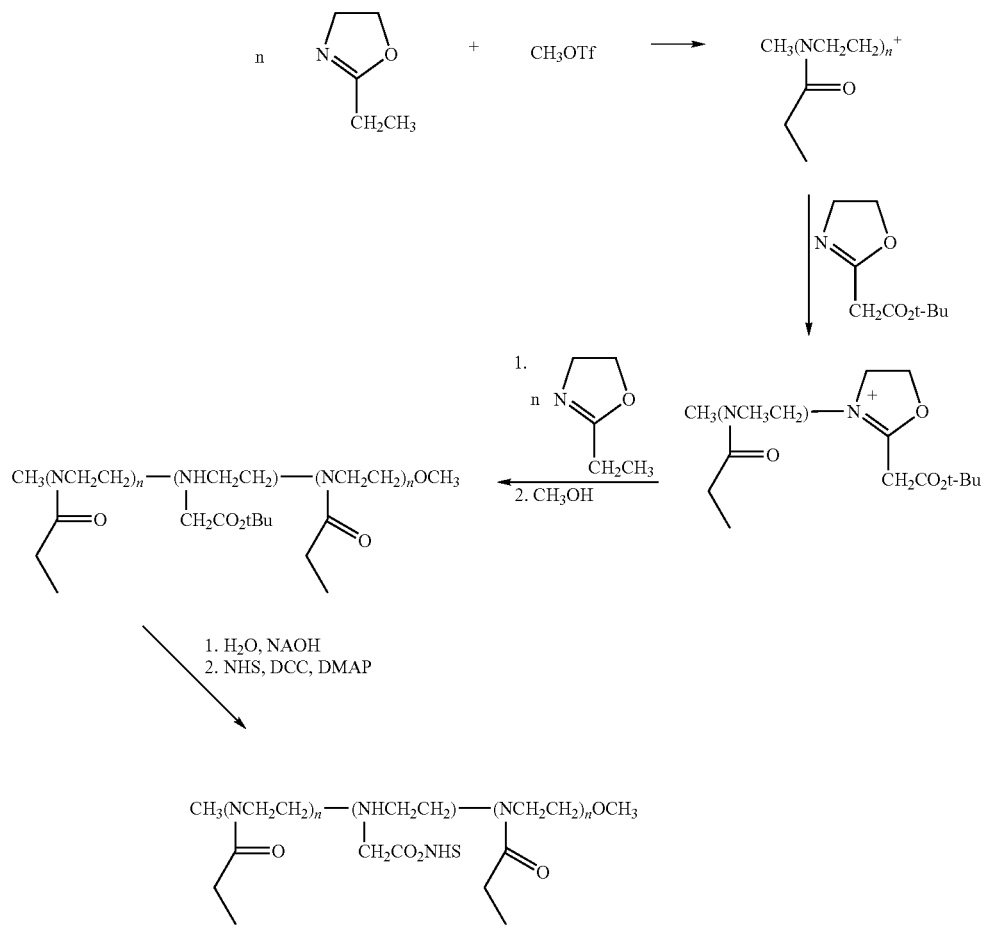

a. Formation of Polymer

To 1 g (0.01 moles) of 2-ethyl-2-oxazoline in 20 ml of dry chlorobenzene under nitrogen at 0° C. is added 0.033 g (0.0002 mole) of methyl triflate with stirring. The mixture is then rapidly heated to 80° C. and heating continued for 6 h. The resulting mixture is cooled to 0° C. and 0.142 g (0.001 moles) of 2-t-butylaceto-2-oxazoline is added and the mixture rapidly heated to 80° C. and held at that temperature for 3 h. The solution is then cooled to 0° C. and 1 g (0.01 moles) of 2-ethyl-2 oxazoline is added. The solution is then rapidly heated to 80° C. and the temperature held for 6 h. After cooling to room temperature, 1 ml of methanol and 0.1 g of sodium methoxide is added and the mixture stirred for 2 h. The chlorobenzene is removed under vacuum and the residue dissolved in 10 ml of methanol. The resulting solution is poured with stirring into 100 ml of ethyl ether and the resulting precipitate collected by decanting the ether. After repeating the precipitation procedure, the solid product is dried under vacuum at 40° C.

b. Conversion to Carboxylic Acid

The product from above is then dissolved in 1N NaOH and stirred 8 h at room temperature. After acidification with 1N HCl, the product is extracted with three 20 ml portions of methylene chloride. The methylene chloride is dried over sodium sulfate and evaporated under vacuum and the residue purified by ion exchange chromatography on DEAE Sepharose.

c. Conversion to NHS Ester

The product is converted to the active NHS ester by dissolving 1 g (0.0001 moles) in 10 ml of acetonitrile, adding (0.206 g) 0.001 moles of DCC and (0.122 g) 0.001 moles of DMAP and stirring at room temperature 8 h. The acetonitrile is evaporated and the product precipitated by addition of 50 ml of ether. The precipitated product is collected by decanting the ether and drying the residue under vacuum at 40° C.

Example 21

Conjugation of Compound 8 with GCSF

The monofunctional POZ-2 derivative 12 prepared above is conjugated to a target molecule, in this example GCSF, as described below. 2.5 mg of GCSF (0.134 µmol, MW=18.6 KDa), dissolved into 1 ml of 0.2 M sodium borate buffer (pH 8.5), is reacted for 60 min at room temperature with 3 equivalents of 12 per amino group on GCSF (a total of 5 lysine plus the α-amine). Under these conditions, the modification occurs primarily at the more exposed nucleophilic amines.

The formation of several conjugates is confirmed by size exclusion HPLC. Size-exclusion HPLC analysis is conducted using an Agilent GF-250 column eluted with an isocratic mobile phase of 0.1 M sodium phosphate, 0.2 M sodium chloride, pH=7.2 and 20% acetonitrile at 0.3 ml/min. The chromatogram shows a broad elution peak corresponding to higher molecular weight GCSF-POZ-2 conjugate conjugates with respect to the native GCSF in agreement with extensive conjugation and increase in mass.

The foregoing description illustrates and describes the methods and other teachings of the present disclosure. Additionally, the disclosure shows and describes only certain embodiments of the methods and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the methods and other teachings of the present disclosure are not intended to limit the exact embodiments and examples disclosed herein. All references cited herein are incorporated by reference as if fully set forth in this disclosure.

What is claimed:

1. An activated polyoxazoline-2 (POZ-2) derivative of the general structure

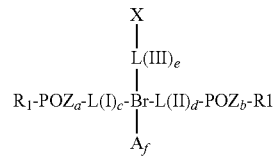

Wherein

POZ$_a$ is a polyoxazoline of formula —[N(COR$_2$)CH$_2$CH$_2$]$_n$—;

POZ$_b$ is a polyoxazoline of formula —[N(COR$_2$)CH$_2$CH$_2$]$_x$—;

L(I), L(II) and L(III) are linking groups;

Br is a branching moiety that is linked with or without a linking group to POZ$_a$, POZ$_b$ and is selected from the group consisting of a nitrogen atom, a substituted or unsubstituted aryl group or a carbon atom, provided that when Br is a carbon atom, at least one of c or d is 1 and the corresponding linking group contains a substituted or unsubstituted aryl group;

X is a functional group which is capable of forming a linkage with a target molecule or being converted to a group that is capable of forming a linkage with a target molecule;

A is a non-reactive group;

R$_1$ is independently selected for each of POZ$_a$ and POZ$_b$ from hydrogen, alkyl, substituted alkyl, aralkyl, or substituted aralkyl group;

R$_2$ is independently selected for each repeating unit of POZ from an unsubstituted or substituted alkyl, alkenyl, alkyl, aralkyl or aryl group;

c, d and e are independently selected from 1 or zero;

f is zero when Br is a nitrogen atom or substituted or unsubstituted aryl group and is 1 when Br is a carbon atom; and n and x are independently selected for each of POZ$_a$ and POZ$_b$ from 3 to 1000.

2. The POZ-2 derivative of claim 1 wherein R$_2$ has from 1 to 12 carbon atoms.

3. The POZ-2 derivative of claim 1 wherein R$_2$ is methyl, ethyl or n-propyl.

4. The POZ-2 derivative of claim 1 wherein at least one of POZ$_a$ and POZ$_b$ of the POZ-2 derivative has a polydispersity value of less than or equal to 1.2, less than or equal to 1.1 or less than or equal to 1.05.

5. The POZ-2 derivative of claim 1 wherein the POZ-2 derivative is a monofunctional POZ-2 derivative.

6. The POZ-2 derivative of claim 1 wherein X is selected from the groups consisting of carboxylic acid, active esters, carbonates, aldehyde, oxyamine, acetylene, isocyanates, isothiocyanate, amines, alcohol, tresylate (2,2,2-trifluorethylsulfonate), vinylsulfone, iodoacetamide, pyridyldisulfide, ketones, azide, hydrazide and maleimide.

7. The POZ-2 derivative of claim 1 wherein the linkage with the target molecule is a hydrolytically stable linkage.

8. The POZ-2 derivative of claim 1 wherein the functional group is protected.

9. The POZ-2 derivative of claim 1 wherein L(I), L(II) and L(III) are each independently selected from —NH—, substituted or unsubstituted alkyl groups or substituted or unsubstituted alkenyl groups.

10. The POZ-2 derivative of claim 1 wherein A is H or a substituted or unsubstituted alkyl group.

11. The POZ derivative of claim 1 wherein Br is a C atom and c is 1 and L(I) contains a substituted or unsubstituted aryl group.

12. The POZ derivative of claim 1 wherein Br is a C atom and c is 1, d is 1 and at least one of L(I) and L(II) contains a substituted or unsubstituted aryl group.

13. A target molecule-POZ-2 conjugate of the general formula A-B-TM, wherein
   A is a POZ-2 derivative of claim 1 minus any leaving groups eliminated during the reaction of the active functional group on the POZ-2 derivative with a binding partner on a target molecule;
   TM is a target molecule, the target molecule containing the binding partner; and
   B is a hydrolytically stable linkage formed between the active functional group and the binding partner.

14. The target molecule-POZ-2 conjugate of claim 13 wherein the active functional group is an Iodoacetamide, the binding partner is SH and B is a thioether linkage, the active functional group is a maleimide, the binding partner is SH and B is a thioether linkage, the active functional group is an active carbonate, the binding partner is $NH_2$ and B is a urethane linkage, the active functional group is an active ester, the binding partner is $NH_2$ and B is an amide linkage or the active functional group is an aldehyde, the binding partner is $NH_2$ and B is an amine linkage.

15. The target molecule POZ-2 conjugate of claim 13 wherein the in vivo half-life of the target molecule-POZ-2 conjugate is increased under physiological conditions.

16. The target molecule POZ-2 conjugate of claim 13 wherein at least one POZ chain of the POZ-2 derivative has a polydispersity value of less than or equal to 1.2, less than or equal to 1.1 or less than or equal to 1.05.

* * * * *